US010488416B2

(12) United States Patent
Brechbuhl et al.

(10) Patent No.: US 10,488,416 B2
(45) Date of Patent: Nov. 26, 2019

(54) TARGETING BREAST CANCER THERAPY BASED ON STROMAL SUBTYPES AND CD146 COMPOSITION

(71) Applicant: The Regents of the University of Colorado, a Body Corporate, Denver, CO (US)

(72) Inventors: Heather Brechbuhl, Commerce City, CO (US); Peter Kabos, Greenwood Village, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 118 days.

(21) Appl. No.: 15/617,709

(22) Filed: Jun. 8, 2017

(65) Prior Publication Data

US 2017/0269088 A1    Sep. 21, 2017

Related U.S. Application Data

(63) Continuation of application No. PCT/US2015/065054, filed on Dec. 10, 2015.

(60) Provisional application No. 62/090,339, filed on Dec. 10, 2014.

(51) Int. Cl.
| | |
|---|---|
| *A61K 31/138* | (2006.01) |
| *G01N 33/574* | (2006.01) |
| *A61K 31/517* | (2006.01) |
| *A61K 31/5377* | (2006.01) |
| *A61K 31/565* | (2006.01) |
| *A61K 39/395* | (2006.01) |
| *A61K 35/33* | (2015.01) |
| *A61K 45/06* | (2006.01) |
| *C07K 16/28* | (2006.01) |
| *C12Q 1/6886* | (2018.01) |

(52) U.S. Cl.
CPC ..... *G01N 33/57415* (2013.01); *A61K 31/138* (2013.01); *A61K 31/517* (2013.01); *A61K 31/5377* (2013.01); *A61K 31/565* (2013.01); *A61K 35/33* (2013.01); *A61K 39/39558* (2013.01); *A61K 45/06* (2013.01); *C07K 16/2863* (2013.01); *C12Q 1/6886* (2013.01); *C12Q 2600/106* (2013.01); *C12Q 2600/158* (2013.01); *G01N 2333/70596* (2013.01); *G01N 2800/52* (2013.01)

(58) Field of Classification Search
CPC .................................................. A61K 31/138
USPC .................................................... 424/130.1
See application file for complete search history.

(56) References Cited

U.S. PATENT DOCUMENTS

| | | |
|---|---|---|
| 2010/0317740 A1 | 12/2010 | Petricoin et al. |
| 2011/0224149 A1 | 9/2011 | Xiao |
| 2013/0034549 A1 | 2/2013 | Harper et al. |

OTHER PUBLICATIONS

Cittelly et al., Downregulation of miR-342 is associated with tamoxifen resistant breast tumors Mol Cancer. 2010. vol. 9: 317.
De Placido et al., Twenty-year Results of the Naples Gun Randomized Trial: Predictive Factors of Adjuvant Tamoxifen Efficacy in Early Breast Cancer. Clinical cancer research. 2003. vol. 9: 1039-1046.
Finak et al., Stromal gene expression predicts clinical outcome in breast cancer. Nature Medicine. 2008. vol. 14 (No. 5): 518-527.
Freund et al., IL-8 expression and its possible relationship with estrogen-receptor-negative status of breast cancer cells. Oncogene. 2003. vol. 22: 256-265.
Gee et al., The Antiepidermal Growth Factor Receptor Agent Gefitinib (ZD1839/Iressa) Improves Antihormone Response and Prevents Development of Resistance in Breast Cancer in Vitro. Endocrinology. 2003. vol. 144 (No. 11): 5105-5117.
Harvey et al., Estrogen receptor status by immunohistochemistry is superior to the ligand-binding assay for predicting response to adjuvant endocrine therapy in breast cancer. Journal of Clinical Oncology. 1999. vol. 17 (No. 5): 1474-1481.
Huber-Keener et al., Differential Gene Expression in Tamoxifen-Resistant Breast Cancer Cells Revealed by a New Analytical Model of RNA-Seq Data. PloS one. 2012. vol. 7 (No. 17): e41333.
Jansen et al., Molecular Classification of Tamoxifen-Resistant Breast Carcinomas by Gene Expression Profiling. Journal of clinical oncology. 2005. vol. 23 (No. 4): 732-740.
Johnston. New Strategies in Estrogen Receptor—Positive Breast Cancer. Clinical Cancer Research. 2010. vol. 16 (No. 7): 1979-1987.
Kabos et al., Patient-derived luminal breast cancer xenografts retain hormone receptor heterogeneity and help define unique estrogen-dependent gene signatures. Breast Cancer Research and Treatment. 2012. vol. 135 (No. 2): 415-432.

(Continued)

*Primary Examiner* — Sean E Aeder
(74) *Attorney, Agent, or Firm* — Smith & Hopen, P.A.; Michael M. McGaw

(57) ABSTRACT

Methods for targeted breast cancer therapy in a subject based upon evaluating the stromal subtypes and CD146 composition in the adjacent tissue. ER+ breast cancers contain two CAF subtypes defined by CD146 expression. $CD146^{neg}$ CAFs suppress ER expression in ER+ breast cancer cells, decrease tumor cell sensitivity to estrogen, switch ER proliferation dependency toward EGFR dependency and decrease tumor cell sensitivity to antiendocrine therapy. Conversely, the presence of $CD146^{pos}$ CAFs enhances ER expression in ER+ breast cancer cells and sustains ER-dependent proliferation and sensitivity to tamoxifen. Co-cultures of $CD146^{pos}$ CAFs with tamoxifen-resistant breast cancer cells restores sensitivity to tamoxifen. Gene expression profiles of patient breast tumors with predominantly $CD146^{neg}$ CAFs correlate with inferior clinical response to tamoxifen and worse patient outcomes. CAF composition contributes to treatment response and patient outcomes in ER+ breast cancer, and provide a target for drug development.

16 Claims, 23 Drawing Sheets

(56) References Cited

OTHER PUBLICATIONS

Kalyuga et al., ELF5 Suppresses Estrogen Sensitivity and Underpins the Acquisition of Antiestrogen Resistance in Luminal Breast Cancer. PLoS Biol. 2012. vol. 10 (No. 12): e1001461.

Ring et al., Mechanisms of tamoxifen resistance. Endocr Relat Cancer. 2004. vol. 11: 643-558.

Mosheni et al., MACROD2 overexpression mediates estrogen independent growth and tamoxifen resistance in breast cancers. PNAS. 2014. vol. 111 (No. 49): 17606-17611.

Oosterkamp et al., USP9X Downregulation Renders Breast Cancer Cells Resistant to Tamoxifen. Cancer research. 2014. vol. 74 (No. 14): 3810-3820.

Pietras and Ostman. Hallmarks of cancer: interactions with the tumor stroma. Experimental Cell Research. 2010. vol. 316: 1324-1331.

Puhalla et al., Hormonal therapy in breast cancer: A model disease fro the personalization of cancer care. Molecular oncology. 2012. vol. 6: 222-36.

Brechbuhl et al. Epidermal growth factor receptor activity is necessary for basal cell proliferation. Am J Physiol Lung Cell Mol Physiol. 2014. vol. 307: L800-L810.

Kabos et al., Cytokeratin 5 positive cells represent a steroid receptor negative and therapy resistant subpopulation in luminal breast cancers. Breast Cancer Res Treat. 2011. vol. 128 (No. 1): 1-19.

Axlund et al., Progesterone-inducible cytokeratin 5 positive cells in luminal breast cancer exhibit progenitor properties. Horm Cancer. 2013. vol. 4 (No. 1): 36-49.

Pillai et al., HITS-CLIP reveals key regulators of Nuclear Receptor signaling in breast cancer. Breast Cancer Res Treat. 2014. vol. 146 (No. 1): 85-97.

Yoo et al., A High-Content Assay to Identify Small-Molecule Modulators of a Cancer Stem Cell Population in Luminal Breast Cancer. J Biomol Screen. 2012. vol. 17 (No. 9): 1211-1220.

Sartorius et al., Estrogen promotes the brain metastatic colonization of triple negative breast cancer cells via an astrocyte-mediated paracrine mechanism. Oncogene. 2016. vol. 35 (No. 22): 2881-2892.

Brechbuhl et al., CD146 positive and negative stroma direct breast tumor estrogen receptor levels, therapeutic response and metastatic potential. Cancer Research. 2015. vol. 75: P4-04-06.

Iwata et al., Functionally and Phenotypically Distinct Subpopulations of Marrow Stromal Cells are Fibroblast in Origin and Induce Different Fates in Peripheral Blood Monocytes. Stem Cells and Development. 2014. vol. 23 (No. 7): 729-740.

Imbert et al., CD146 Expression in Human Breast Cancer Lines Inducts Phenotypic and Functional Changes Observed in Epithelial to Mesenchymal Transition. PLoS ONE. 2012. vol. 7 (No. 8): e43752.

International Search Report for PCT/US2015/065054 (filing date: Dec. 10, 2015) dated Feb. 23, 2016; Applicant: The Regents o the University of Colorado, A Body Corporate.

International Preliminary Report on Patentability for PCT/US2015/065054 (filing date: Dec. 10, 2015) with a priority date of Dec. 10, 2014; Applicant: The Regents of the University of Colorado, A Body Corporate et al.

Lozowoski et al., Estrogen Receptor Determination in Fine Needle Aspirates of the Breast: Correlation with Histologic Grade and Comparison with Biochemical Analysis. Acta cytologica. 1987. vol. 31 (No. 5): 557-62.

Hierarchical Clustering Analysis

| CD146+ Fibroblasts | | CD146- Fibroblasts | |
|---|---|---|---|
| Normal Breast Stroma | Tumor-Associated Breast Stroma | Normal Breast Stroma | Tumor-Associated Breast Stroma |
| 1 | 6 | 0 | 52 |

*FIG. 3*

TARGETING BREAST CANCER THERAPY BASED ON STROMAL SUBTYPES AND CD146 COMPOSITION

CROSS-REFERENCE TO RELATED APPLICATIONS

This application is a continuation of International Patent Application No. PCT/US2015/065054, entitled "TARGETING BREAST CANCER THERAPY BASED ON STROMAL SUBTYPES AND CD146 COMPOSITION", filed Dec. 10, 2015, which claims the benefit of U.S. Provisional Patent Application No. 62/090,339, entitled "TARGETING BREAST CANCER THERAPY BASED ON STROMAL SUBTYPES AND CD146 COMPOSITION", filed Dec. 10, 2014.

FIELD OF INVENTION

This invention relates to cancer screening and treatment. More specifically, this invention relates to targeted breast cancer treatment in a subject responsive to the cancer associated fibroblasts subtypes and the CD146+ composition in the stroma of the subject.

BRIEF DESCRIPTION OF THE RELATED ART

Estrogen receptor (ER) expression is the primary prognostic and predictive biomarker for patients with breast cancer. Its presence defines the luminal breast cancer subtypes (A and B) and delineates candidacy for anti-endocrine therapy, which significantly improves survival outcomes (Lozowski, M S, et al., *Acta cytologica.* 1987; 31(5):557-62; Puhalla, S, et al., *Molecular oncology.* 2012; 6(2):222-36). Breast cancers, however, commonly display high heterogeneity of ER expression, where individual cells within a tumor vary in their level of ER expression. The fact that a majority of ER+ tumors contain a range of cells from ER− to ER+, led to development of the Allred score for ER positivity based on overall ER presence and intensity in an individual tumor (Harvey, J M, et al., *Journal of Clinical Oncology: Official Journal of the American Society of Clinical Oncology.* 1999; 17(5):1474-81). Clinical presentation of only one percent ER positive tumor cells justifies the use of adjuvant anti-endocrine therapy. However, development of anti-endocrine resistance remains a major clinical problem that occurs in 40 percent of patients (Ring, A, and Dowsett, M. *Endocr Retat Cancer.* 2004; 11(4):643-58). Recurrent tumors do not typically demonstrate complete loss of ER expression (Kuukasjarvi, T, et al., *Journal of Clinical Oncology: Official Journal of the American Society of Clinical Oncology.* 1996; 14(9):2584-9), rather they show a combination of both loss of ER expression and ER growth dependency.

To date, it remains unclear how individual tumors maintain a balance of ER positive and negative cells. Intrinsic cellular factors do not fully explain the range in ER expression within a single tumor. Recent evidence demonstrates that the tumor microenvironment, defined as the stroma and extracellular matrix immediately adjacent to cancer cells, plays a prominent role in all aspects of cancer biology including tumorigenesis, cancer progression and metastasis formation (Pietras, K and Ostman, A, *Experimental Cell Research.* 2010; 316(8):1324-31). In fact, gene expression signatures from breast cancer-associated stroma have been shown to accurately predict clinical outcomes in breast cancer patients equally well as signatures derived from whole breast tumors (Finak G., et al. Stromal gene expression predicts clinical outcome in breast cancer. *Nature Medicine.* 2008; 14(5):518-277).

Anti-endocrine therapy remains the most effective treatment for ER+ breast cancer, but development of resistance is a major clinical complication. Effective targeting of mechanisms controlling loss of ER dependency has been elusive.

SUMMARY OF THE INVENTION

The present invention demonstrates a differential response to treatment based on adjacent stromal components. The response of cancers to therapy can be deduced from differences in the stromal subtypes, such as between 146+/− stroma in gene expression profiling, which leads to a difference in expressed cellular and excreted proteins.

Accordingly, the present work opens numerous avenues for the treatment and targeted therapy of cancers, including breast cancer, based upon stromal subtypes and CD146 composition. In a first aspect the present invention provides a first method of treating cancer in a subject. The method according to the first aspect includes the steps of providing a sample containing the stroma from the cancerous tissue of the subject, screening the sample to evaluate the CD146(+)-to-CD146(−) ratio of fibroblasts in the stroma, and administering anti-endocrine therapy to the subject responsive to the detection of a high proportion of CD146(+) fibroblasts in the sample relative to a control. Alternatively, a high proportion of CD146(+) fibroblasts could be about 60% or higher, while a low proportion of CD146(+) fibroblasts could be about 20% or lower. In an advantageous embodiment the cancer is breast cancer. Because CD146$^{neg}$ fibroblasts promote EGFR dependent proliferation, all cancers with a prominent CD146$^{neg}$ CAF component should benefit from EGFR therapy. The anti-endocrine therapy can be a compound selected from the group consisting of tamoxifen, everolimus, palbociclib and fulvestrant.

In a second aspect the present invention provides a second method of treating cancer in a subject. The method according to the second aspect includes the steps of providing a sample containing the stroma from the cancerous tissue of the subject, screening the sample to evaluate the CD146(+)-to-CD146(−) ratio of fibroblasts in the stroma, and administering estrogen therapy to the subject responsive to the detection of a high proportion of CD146(+) fibroblasts in the sample. In an advantageous embodiment the cancer is breast cancer.

In a third aspect the present invention provides a third method of treating cancer in a subject. The method according to the third aspect includes the steps of providing a sample containing stroma from the cancerous tissue of the subject, screening the sample to evaluate the CD146(+)-to-CD146(−) ratio of fibroblasts in the stroma, and administering a TGFβ inhibitor to the subject responsive to the detection of a high proportion of CD146(+) fibroblasts in the sample. In an advantageous embodiment the cancer is breast cancer.

In a fourth aspect the present invention provides a fourth method of treating cancer in a subject. The method according to the fourth aspect includes the steps of providing a sample containing stroma from the cancerous tissue of the subject, screening the sample to evaluate the CD146(+)-to-CD146(−) ratio of fibroblasts in the stroma, and administering an EGFR inhibitor to the subject responsive to the detection of a high proportion of CD146(−) fibroblasts in the sample. In an advantageous embodiment the cancer is breast cancer. The EGFR inhibitor can be gefitinib, erlotonib or cetuximab.

In a fifth aspect the present invention provides a fifth method of treating cancer in a subject. The method according to the fifth aspect includes the steps of providing a sample containing stroma from the cancerous tissue of the subject, screening the sample to evaluate the cancer associated fibroblast subtype composition of the stroma, and administering cancer therapy to the subject responsive to the profile of cancer associated fibroblasts in the screened stroma. In an advantageous embodiment the cancer is breast cancer.

BRIEF DESCRIPTION OF THE DRAWINGS

For a fuller understanding of the invention, reference should be made to the following detailed description, taken in connection with the accompanying drawings, in which:

FIG. 3 is a figure depicting gene signature analysis. CD146+ CAFs cluster with normal breast stroma, compared to CD146− CAFs which cluster with breast tumor associated stroma.

FIGS. 6A-6D illustrate the influence from CD146$^{neg}$ fibroblasts produces an epithelial signature that is predictive of decreased recurrence-free survival in tamoxifen treated patients. *p<0.001; **p<0.0001.

FIG. 6B is a graph illustrating the tamoxifen treated validation set. Patient validation set demonstrating significant predictive power of increased recurrence-free survival in patients with the CD146$^{pos}$ signature. *p<0.001; **p<0.0001.

FIG. 6C is a graph illustrating the untreated patient training set. The CAF influenced gene signature is not predictive of recurrence-free survival in patients who were not treated with tamoxifen, demonstrating that the signature is specific to tamoxifen response.

FIG. 6D is a graph illustrating the tamoxifen treated validation set. Inclusion of 37 genes predicted in literature to be involved in estrogen responsiveness and/or tamoxifen resistance are not predictive of recurrence-free survival, demonstrating that our CAF influenced signature is unique.

DETAILED DESCRIPTION OF THE PREFERRED EMBODIMENT

Figure 1A:
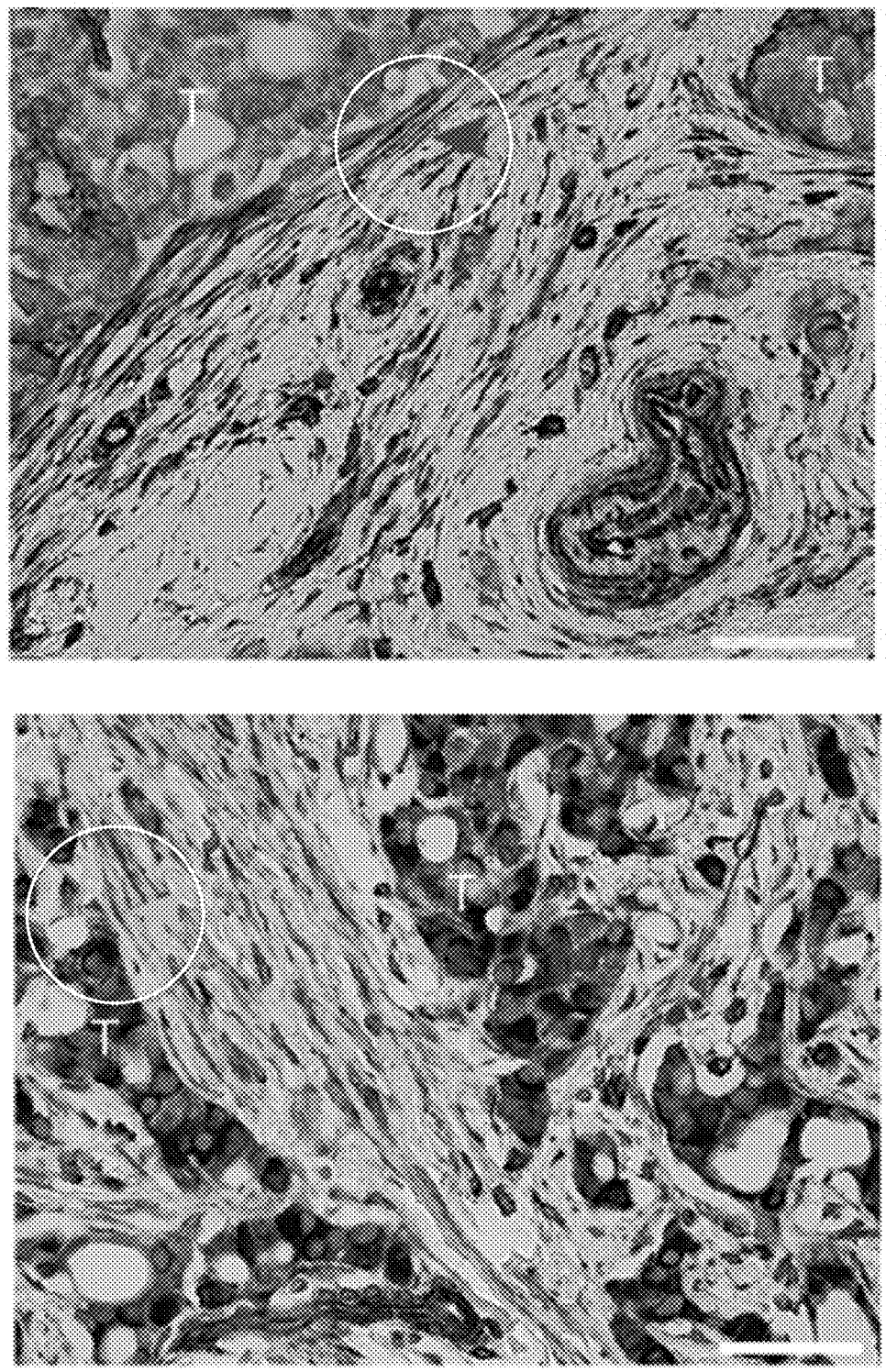
FIG. 1A is a pair of photographs reproduced in gray scale showing immunohistochemistry staining of patient tissue demonstrating the presence of both $CD146^{pos}$ (upper image 1A, vector red stain, dark gray arrowhead within white circle) and $CD146^{neg}$ (lower image 1A, DAB stain, light gray arrowhead within white circle) stroma. Two subtypes of fibroblasts are present in normal and breast cancer associated stroma based on CD146 expression and increased ratios of $CD146^{pos}$ fibroblasts correlates with high ER expression. Patients with Allred scores equal to 8 had a mean of 68% $CD146^{pos}$ stroma, whereas patients with Allred scores less than 8 had a mean of 18% $CD146^{pos}$ stroma. The Allred score is a combined measure of the percent of positive ER breast cancer cells and the intensity of their positivity. Scale bars: 20 µm. T, tumor; V, endothelial vessels.

Estrogen receptor (ER) positive disease is the most common breast cancer subtype. Targeting of ER is an effective therapy, but development of anti-endocrine resistance remains a major cause of treatment failure. Attempts to uncover and therapeutically target mechanisms of anti-endocrine resistance have focused mainly on tumor intrinsic traits. Two subtypes of cancer-associated fibroblasts (CAFs) are identified herein, based on their CD146 expression. Those CAF subtypes differentially contribute to tumoral ER expression and tamoxifen resistance or sensitivity as shown in the present disclosure. Furthermore, CAFs can enforce ER or epidermal growth factor (EGF) dependent tumor growth and predict treatment response and patient outcomes. These findings have direct clinical implications and help explain the disappointing results of early phase trials with EGF receptor inhibitors in ER+ breast cancer. Insight into CAF-tumor interactions and recognition of CAF subtypes in breast cancer facilitate a personalized approach to therapy.

Anti-endocrine therapy remains the most effective treatment for ER+ breast cancer, but development of resistance is a major clinical complication. Effective targeting of mechanisms controlling loss of ER dependency remains elusive. Breast cancer associated fibroblasts (CAFs), the largest component of the tumor microenvironment, were analyzed as a factor contributing to variation in ER expression and anti-endocrine resistance.

Tissues from ER+ breast cancer patients were analyzed for the presence of CD146 positive (CD146$^{pos}$) and CD146 negative (CD146$^{neg}$ fibroblasts. ER dependent proliferation and tamoxifen sensitivity was evaluated in ER+ tumor cells cultured with CD146$^{pos}$ or CD146$^{neg}$ fibroblasts. RNAseq was used to develop a high confidence gene signature predicting for disease recurrence in tamoxifen treated patients with ER+ breast cancer.

ER+ breast cancers contain two CAF subtypes defined by CD146 expression, as shown herein. CD146$^{neg}$ CAB suppress ER expression in ER+ breast cancer cells, decrease tumor cell sensitivity to estrogen, switch ER proliferation dependency toward EGFR dependency and decrease tumor cell sensitivity to antiendocrine therapy. We propose that breast cancer patients presenting with increased presence of CD146$^{neg}$ CAFs, will benefit from treatment with EGFR inhibitors. Conversely, the presence of CD146$^{pos}$ CAFs enhances ER expression in ER+ breast cancer cells and sustains ER-dependent proliferation and sensitivity to tamoxifen. Co-cultures of CD146$^{pos}$ CAFs with tamoxifen-resistant breast cancer cells restores sensitivity to tamoxifen. We are propose that pharmacological manipulation of CAFs that increase the proportion of CD146$^{pos}$ CAFs will promote or restore efficacy of antiendocrine therapy. Gene expression profiles of patient breast tumors with predominantly CD146$^{neg}$ CAFs correlate with inferior clinical response to tamoxifen and worse patient outcomes. The data presented herein shows that CAF composition contributes to treatment response and patient outcomes in ER+ breast cancer, and should be considered a target for drug development.

Fibroblasts represent the most abundant stromal cell type and, in addition to immune and endothelial cells, they can influence tumor biology (Metros, K and Ostman, A, *Experimental Cell Research* 2010; 316(8):1324-31). Fibroblasts also constitute the largest component of the tumor microenvironment and are traditionally classified as normal (NF) or cancer associated (CAF) based on the distance from malignant tissue and the presence of proteins associated with activated fibroblasts and myofibroblasts.

This study first examines some subtypes of CAFs existing in breast tissue and provides links to their important functional roles in determining responsiveness of breast cancer cells to estrogen. Stromal fibroblasts are heterogeneous in their function and expression profile. CD146 (MCAM) is a stromal cell surface marker defining hematopoietic stem cell-niche associated fibroblasts. All tissue stromal fibroblasts are mesenchymal in origin. We reasoned that breast fibroblasts also contain both CD146$^{pos}$ and CD146$^{neg}$ fibroblasts, and that CD146 expression defines functional subsets of CAFs. It is demonstrated herein that cues from fibroblast subtypes, as defined by CD146 expression, influence ER expression and treatment response of ER+ breast cancers. It is further shown that the ratio of CD146$^{pos}$/CD146$^{neg}$ stromal subtypes correlates with ER expression in patient samples. Finally, a gene signature was generated that accurately and uniquely predicts recurrence-free survival rates in tamoxifen treated patients based on influence from the defined stromal subtypes. Taken together, there exists a hierarchical organization in tumor-associated stroma, based upon CD146 expression, with implications for disease progression and therapeutic sensitivity. Patients with a tumor signature influenced by CD146$^{pos}$ CAFs should be treated with standard anti-endocrine therapy. However, patients with a tumor signature influenced by CD146$^{neg}$ CAFs should be considered higher risk and treated more aggressively.

The understanding of tumor cell biology was greatly enhanced through the recognition that non-tumor derived stromal cells, such as T-helper cells and macrophages, influence tumor progression and response to therapy. The results presented herein demonstrate how functionally distinct subtypes of cancer-associated fibroblasts can directly affect ER expression and growth dependency in luminal breast cancers. The described CAF subtypes likely represent extremes of cellular phenotypes that can be found in a tumor. These in vitro studies, in vivo studies, and analysis of clinical samples, provide compelling evidence that absence of CD146 expressing CAFs is associated with a more aggressive tumor phenotype in breast cancer patients based in part on loss of ER growth dependency and gain of EGFR growth dependency. Development of anti-endocrine resistance is associated with activation of EGFR signaling, a fact that prompted several clinical trials with EGFR tyrosine kinase inhibitors in ER+ breast cancer patients as a way to delay endocrine resistance (Gee, J M, et al., *Endocrinology.* 2003; 144(11):5105-17). Unfortunately, these trials had mixed results and demonstrated very limited patient benefit (Johnston, S R. Clinical Cancer Research: An Official Journal of the American Association for Cancer Research. 2010; 16(7):1979-87). The data presented herein indicate that therapeutic strategies, which include consideration of signaling factors produced by CAFs, and other cells within the microenvironment, are necessary for personalization of care, improved treatment efficacy and outcomes.

Specifically in luminal breast cancers, ER serves as both a prognostic and predictive marker in patients and forms the basis of clinical decision-making (Lozowski, M S, et al., *Acta cytologica.* 1987; 31(5):557-62; Puhalla, S, et al., *Molecular oncology.* 2012; 6(2):222-36). Although luminal (ER+) breast cancers have overall better prognosis (Finak G., et al. Stromal gene expression predicts clinical outcome in breast cancer. Nature Medicine. 2008; 14(5):518-27; Kalluri, R and Zeisberg M. *Nature Reviews Cancer,* 2006; 6(5):392-401) luminal disease still accounts for most breast cancer related deaths due to its prevalence (Knutson K L and Disis M L. *Cancer Immuno Immunother.* 2005 54(8):721-8). Short of eradicating ER+ disease at diagnosis, efficacy of treatment is limited by development of antiendocrine resistance that leads to treatment failure and disease recurrence or progression. In fact, the data herein demonstrates that tumor ER heterogeneity is, in part, defined by CAF subtypes, and that CAF subtypes can influence tumor response to anti-endocrine therapy. Development of tamoxifen resistant cell lines, such as TAMR-1 cells, requires escalating doses and long treatment agent exposure periods (up to one year) (Kilker R L et al. J Steroid Biochem Mol Biol. 2004; 92(1-2):63-71; Madsen M W, et al. Mol Cell Endocrinol. 1995; 109(2)197-207); strikingly, it is shown herein that a similar phenotype can be achieved by a short co-culture (five days) with CD146$^{neg}$ CAFs. Equally important, the tamoxifen resistant phenotype can be tampered by a short co-culture with CD146$^{pos}$ CAFs. These data strongly support the need to consider CAFs in order to further elucidate the mechanisms of anti-endocrine resistance. As proof of principle, an epithelial gene signature enforced by CAF subtypes is identified that accurately predicted recurrence free survival in tamoxifen treated patients.

This data presents a new paradigm for considering CAFs as a heterogeneous population that has significant impact on tumor behavior based on the predominant subtype. Whether the ratio of CD146$^{pos}$/CD146$^{neg}$ cells is host dependent is not known. Recruitment of stromal components to tumors has been observed and it is therefore conceivable that some tumors are more apt at recruiting distant stroma into the microenvironment than others. Furthermore, it is unclear if recruited CAFs have a given CD146 phenotype/signature prior to arriving or if this is a programmable state.

It is shown herein that CAFs do not represent a homogeneous cell population, but contain at least two distinct cellular subtypes that differentially influence breast cancer cells with respect to their molecular characteristics, phenotypic behavior in disease progression, and markers of therapeutic response. This data supports the hypothesis that tumors hijack normal stromal components of the tissue microenvironment and use it to their advantage. The generation of CAF cell lines and their study with a broader range of metastatic transplant models provides a model system to functionally define the breast cancer microenvironment. Studies of CAF biology and improved targeting of their interactions with tumor cells, such as in the present disclosure, enhance our ability to deliver personalized therapy.

Example 1—Materials and Methods

Cell Culture and Drug Treatment:

The human MCF-7 (p53 wildtype, ER-positive, luminal cell) breast cancer cell lines were cultured in Modified Eagle's Medium (MEM) supplemented with 5% fetal calf serum (FCS), nonessential amino acids, L-glutamine, and HEPES buffer at 37° C. with a 5% CO2/95% atmospheric air. Human Stromal cell lines HS5, HS27A, UCD12 and T47D cells were grown in RPMI-1640 supplemented with 5% Fetal Calf Serum (FCS), nonessential amino acids, Penicillin (100 U/ml) and streptomycin (100 mg/mL), CD146 CAF subtypes are genetically and functionally akin to HS27a and HS5 fibroblasts, however, unlike the HS27a and HS5 fibroblast cell lines, our CAFs have a limited number of passages before they become senescent. Therefore, we used HS27a and HS5 fibroblasts in most of our studies and used our primary CAFs to verify our findings in a select set of studies. Unless otherwise indicated by the designation of CAF, described studies utilized HS27a and HS5 fibroblasts.

For experiments testing estrogen or anti-endocrine effects, estrogen positive cells were grown in phenol red-free media with 5% dextran-coated charcoal-stripped FCS for 1-3 days prior to drug treatments. For hormone therapy, cultures were either supplemented with 10 nM 17-β-estradiol or ethanol vehicle alone. For proliferation experiments, cultures were supplemented with 100 nM 4-hydroxy-tamoxifen (tamoxifen), 10 μM gefitinib or ethanol vehicle control. For conditioned media experiments, estrogen free media was conditioned on a confluent layer of fibroblasts or ER+ epithelial tumor cells for 24 hours. Tumor cells were seeded in 96-well plates at a density of 3,000 cells per well in complete media and allowed to attach for 24 hours. The media was changed to conditioned media (65% conditioned media, 35% fresh estrogen free complete media) supplemented with ethanol vehicle, estrogen or estrogen plus tamoxifen.

Immunocytochemistry:

Standard immunocytochemistry (ICC) and immunohistochemistry (IHC) techniques were used. For ICC cells were fixed in either 1 ml cold 4% paraformaldehyde for 20 minutes or ice cold 100% methanol. For antigen retrieval was performed in 10 mM citric acid buffer prior to blocking. Standard staining procedures were followed according to manufacturer recommendations for each antibody. Estrogen receptor alpha (D8H8) rabbit mAb, Vimentin and CD146 were purchased from Cell Signaling Technology (Danvers, Mass.). CK18 mouse mAb was purchased from DAKO (Carpinteria, Calif.). Secondary antibodies were anti-mouse and anti-rabbit Alexa Fluors 488 (green) and 594 (red)-conjugated, respectively and purchased from Jackson ImmunoResearch Laboratories Inc. (West Grove, Pa.). A Nikon E600 microscope was used for photography. Images were merged in Photoshop. ImageJ software was used to analysis human tissue for the percentage of CD146 to vimentin positive stroma. Endothelial vessels and tumor tissue was excluded by drawing around the region and using ImageJ cropping function. Results are reported as the ratio of the pixel density for CD146 staining versus vimentin staining.

Proliferation Assays:

Proliferation was measured by total protein sulforhodamine assay (SRB) or by live cell imaging. Cells were processed for the sulforhodamine B colorimetric (SRB) assay 72 hours after treatment. Briefly, culture media was removed and cells were gently washed 1× with PBS followed by a 30-minute incubation at 4° C. in 10% trichloroacidic acid. Cells were washed 5 times with deionized water and plates were dried for 2 hours. Sulforhodamine B (0.2%) dye was added for 20 minutes at room temperature, followed by 5 washes with 1% acetic acid and a 2-hour drying period. Each well of a 96-well plate received 0.2 mL of 10 mM unbuffered tris base and was agitated for 10 minutes. Total protein was assessed using a BioTek (Winooski, Vt.) Synergy 2 microplate reader (565 nm-690 nm background). Live cell imaging analysis was completed using the Essen BioScience IncuCyte Zoom (Ann Arbor, Mich.) and analyzed using the IncuCyte associated software.

Generation of Cancer Associated Fibroblasts: Normal and tumor tissue samples were collected from patients at the University of Colorado Denver in accordance with IRB approved protocol. The tissue was collected into ice cold DMEM/F12 until ready for processing. Finely minced tissue was placed in collagenase digestion buffer (DMEM/F12 with 10 mM Hepes, 2% BSA, 5 μg/ml Insulin, 0.5 mg/ml hydrocortisone, 300 U/ml collagenase IV (1 mg/ml) and 100 U/ml hyaluronidase) overnight on a rotator at 37° C. Digestion buffer was used at a volume of 10 ml per 1 g of tissue.

Following digestion, any oil layer was gently aspirated off (common to normal breast tissue) and the sample was filtered through a 100 μm mesh into a 50 ml conical tube and centrifuged 1000×g, at 4° C. for 5 minutes to pellet the cells. The cell pellet was re-suspended in 10 ml of PBS and filtered through a 40 μm mesh into a new 50 ml conical tube. Differential centrifugation was used to enrich for stromal cell types. A slow speed, 80×g, 4° C. for 4 minutes, was used to pellet epithelial cells. The supernatant was collected for a second centrifugation step, 100×g, 4° C. for 10 minutes. The resulting pellet is enriched for stromal cells and is re-suspended in DMEM/F12, 5% FBS, NEAR, and Pen/Strep and cultured in standard cell culture flasks. Confluent cell cultures were immortalized with E6E7 virus as described previously (Roecklein, Torok-Storb Blood 1995). Following selection of transduced cells with G418, limiting dilution and clonal selection was used to generate CD146+ and CD146− subtypes from each patient sample. CD146 expression was verified by flow cytometry. Briefly, normal and tumor tissue derived from patient samples were collected and processed as described above in order to obtain single cell suspensions. After pelleting the cells were re-suspended in PBS with 2% FBS and stained with anti-CD146 (Ebiosciences, San Diego, Calif.) and appropriate isotype controls. Flow cytometry analysis was completed at the University of Colorado Cancer Center using a Beckman Coulter Gallios analyzer.

Gene Expression:

Cells were lysed in QIAzol lysis reagent (Qiagen, Valencia, Calif.) and total RNA was isolated using the RNeasy kit (Qiagen, Valencia, Calif.). For Affymetrix gene expression analysis, samples were prepared according to manufacturer guidelines and loaded onto HuGene1.1 ST or HuGene1.0ST and processed by the University of Colorado Genomics and Micorray Core, (Aurora, Colo.). Samples for RNAseq were prepared using a Tru-seq compatible strand-specific, olgio-d(T) selected library construction method and analyzed at the University of Colorado Genomics and Microarray Core, (Aurora, Colo.) on an Illumina HighSeq 2500 (San Diego, Calif.).

Animal Experiments:

All animal experiments were conducted in an AAALAC accredited facility at the University of Colorado Denver under an IACUC approved protocol. MCF-7 tumors labeled with ZS-green were established by injecting 1×10^6 cells into the mammary fat pad of NOD scid gamma (NSG) female and male mice. HS27a or HS5 cells were mixed with the tumor cells at a 1:1 ratio (N=3 mice per stroma subtype). Tumors were allowed to grow for 5 weeks prior to removal. All tumors were supported with estrogen supplementation throughout the study, as previously described (Kabos, P, et al., *Breast Cancer Research and Treatment*. 2012; 135(2): 415-32).

Statistical Analysis:

Statistical analysis was completed using R-package software for the gene expression data sets and with GraphPad Prism 6 analytical software (La Jolla, Calif.) for all other experiments. For single comparisons we used unpaired two-tailed t-test with assumptions of parametric distribution Gaussian distribution and equal standard deviations. For multiple comparisons we used ordinary one-way ANOVA analysis with Tukey multiple comparisons test. Significance was set at $p<0.05$. All cell culture experiments consisted of at least N=4 or more and were repeated at least once using the same ER+ cell type or a separate ER+ cell type. Our in vivo experiment consisted of N=3 animals per stromal subtype. Outliers were considered to be 2 standard deviations from the mean and data are presented as mean+/- the standard error of the mean. Human samples were collected under an approved COMIRB protocol.

Figure 1B:
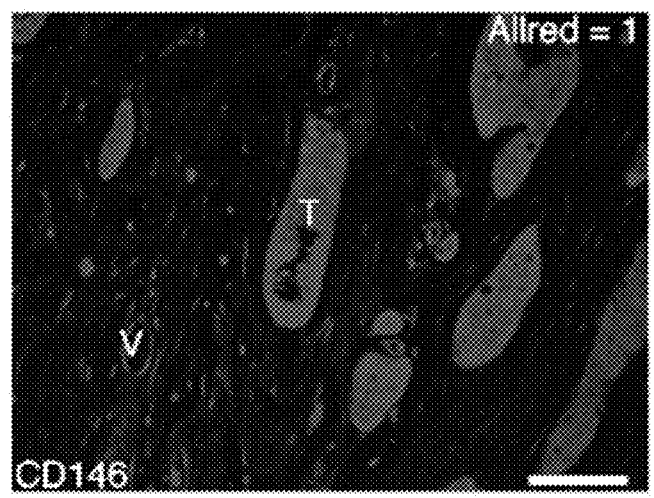
FIG. 1B is a set of three photographs reproduced in gray scale showing immunofluorescence staining of tissue from ER+ breast cancer patients demonstrating a decreased ratio of $CD146^{pos}$ (red stain appearing light gray in grayscale and comparing the upper image in FIG. 1B to the upper image in FIG. 1C) to vimentin (B-C, green stain appearing light gray in grayscale and comparing the middle image in FIG. 1B to the middle image in FIG. 1C) expressing stroma in patients with low Allred (B) compared to high Allred (C) scores (FIG. 1B represents low Allred score, while FIG. 1C represents high Allred score). Scale bars: 20 µm. T, tumor; V, endothelial vessels.
Figure 1B:
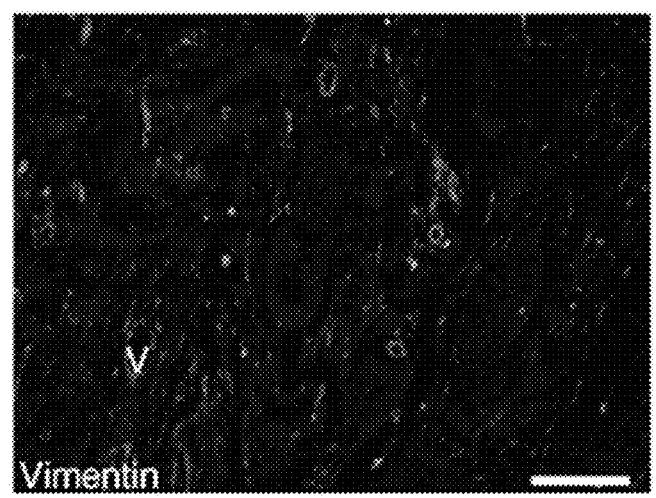
Figure 1B:
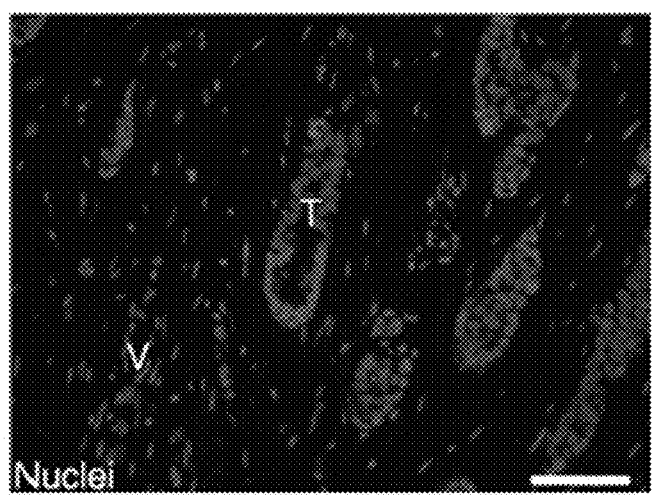
Figure 1C:
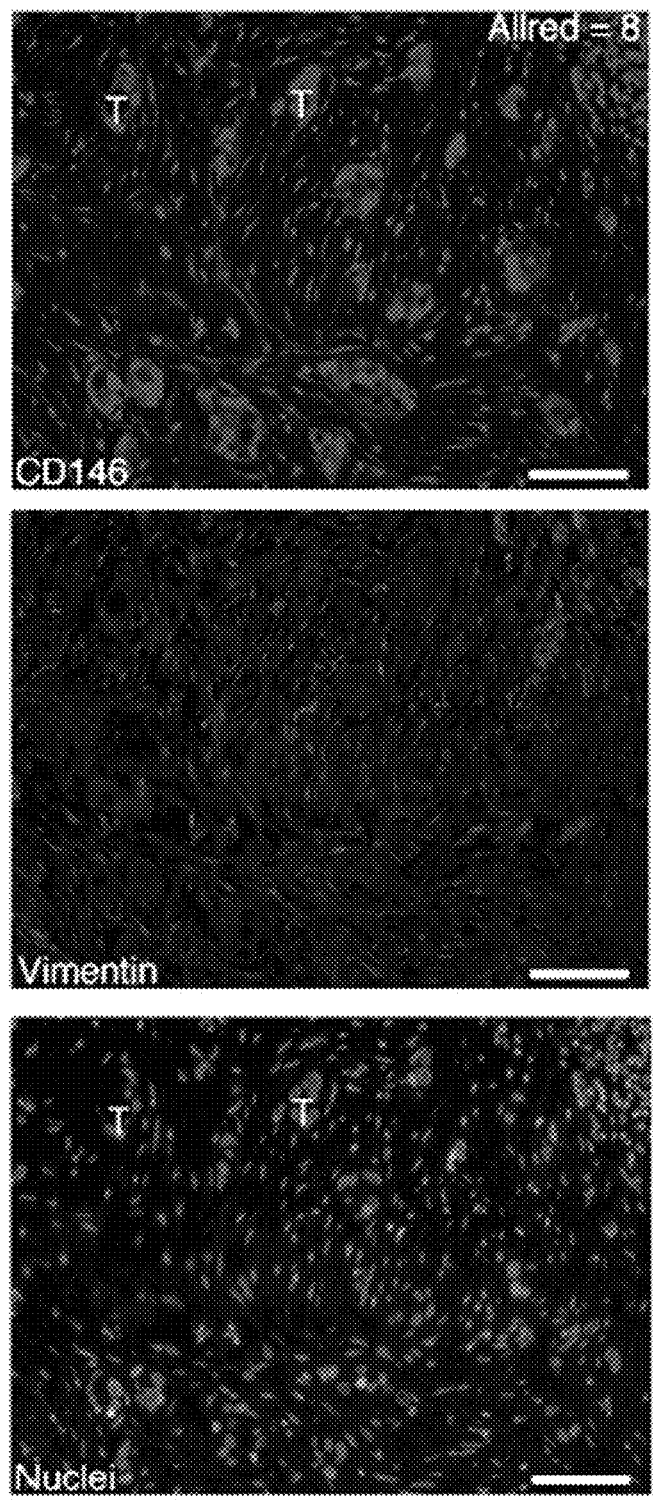
FIG. 1C is a set of three photographs reproduced in gray scale showing immunofluorescence staining of tissue from ER+ breast cancer patients demonstrating a increased ratio of $CD146^{pos}$ (red stain appearing light gray in grayscale and comparing the upper image in FIG. 1B to the upper image in FIG. 1C) to vimentin (B-C, green stain appearing light gray in grayscale and comparing the middle image in FIG. 1B to the middle image in FIG. 1C) expressing stroma in patients with low Allred (B) compared to high Allred (C) scores (FIG. 1B represents low Allred score, while FIG. 1C represents high Allred score). Scale bars: 20 µm. T, tumor; V, endothelial vessels.
Figure 1D:
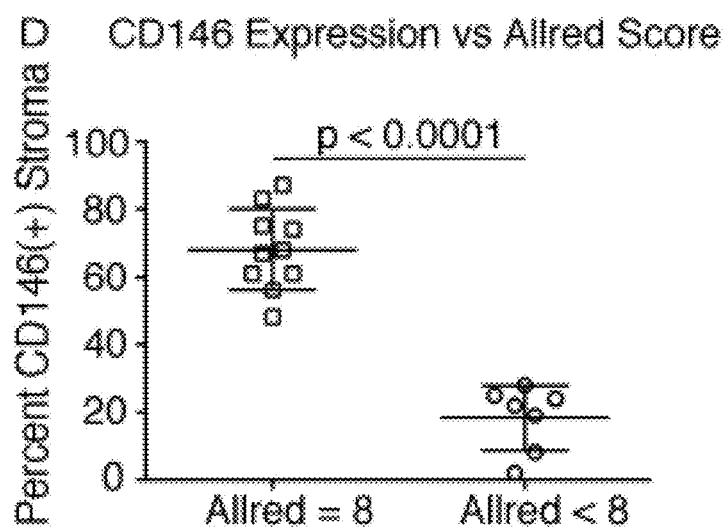
FIG. 1D is a graph depicting a quantification demonstrating that patients with Allred=8 have significantly increased $CD146^{pos}$ stroma compared to Allred<8.

Example 2—CD146 Expression Identifies Subtypes of Normal and Cancer Associated Stroma in Breast Tissue To determine the prevalence of $CD146^{pos}/CD146^{neg}$ cells in breast cancer associated stroma, dual immunohistochemistry (IHC) staining was used with the pan stromal marker vimentin and CD146. The stromal component of ER+ breast cancer associated patient tissues contains mixed populations of $CD146^{pos}$ and $CD146^{neg}$ cells (FIG. 1A). In fact, the staining revealed striking differences in the intensity and frequency of $CD146^{pos}$ stroma between patient samples. This difference by immunofluorescence (IF) staining for CD146 and vimentin was quantified in a cohort of 17 patient samples previously scored by a board certified pathologist for ER expression; ten samples had Allred scores of 8 (high ER) and seven had scores of less than 8 (lower ER). The percentage of CD146 expressing stroma was determined by normalizing to vimentin expression. In addition to marking advanced tumor cells and pericytes, which surround endothelial vessels (Li Q, et al. *The Journal of Pathology.* 2003; 201(2):296-302), 2-87% of the stained cells were vimentin+/$CD146^{neg}$ and vimentin+/$CD146^{pos}$. To quantify this component, tumor epithelial cells and pericytes were manually excluded and the ratio of $CD146^{neg}/CD146^{pos}$ cancer associated stroma to Allred scores for ER was compared. The presence of $CD146^{pos}$ stroma correlated positively with high ER expression (FIGS. 1B and 1C). Patients with Allred scores equal to 8 had a mean of 68% CD146pos stroma, whereas patients with Allred scores less than 8 had a mean of 18% $CD146^{pos}$ stroma (FIG. 1D). These data imply that threshold expression for breast tumor ER is linked to the majority microenvironment fibroblast subtype.

Figure 1E:
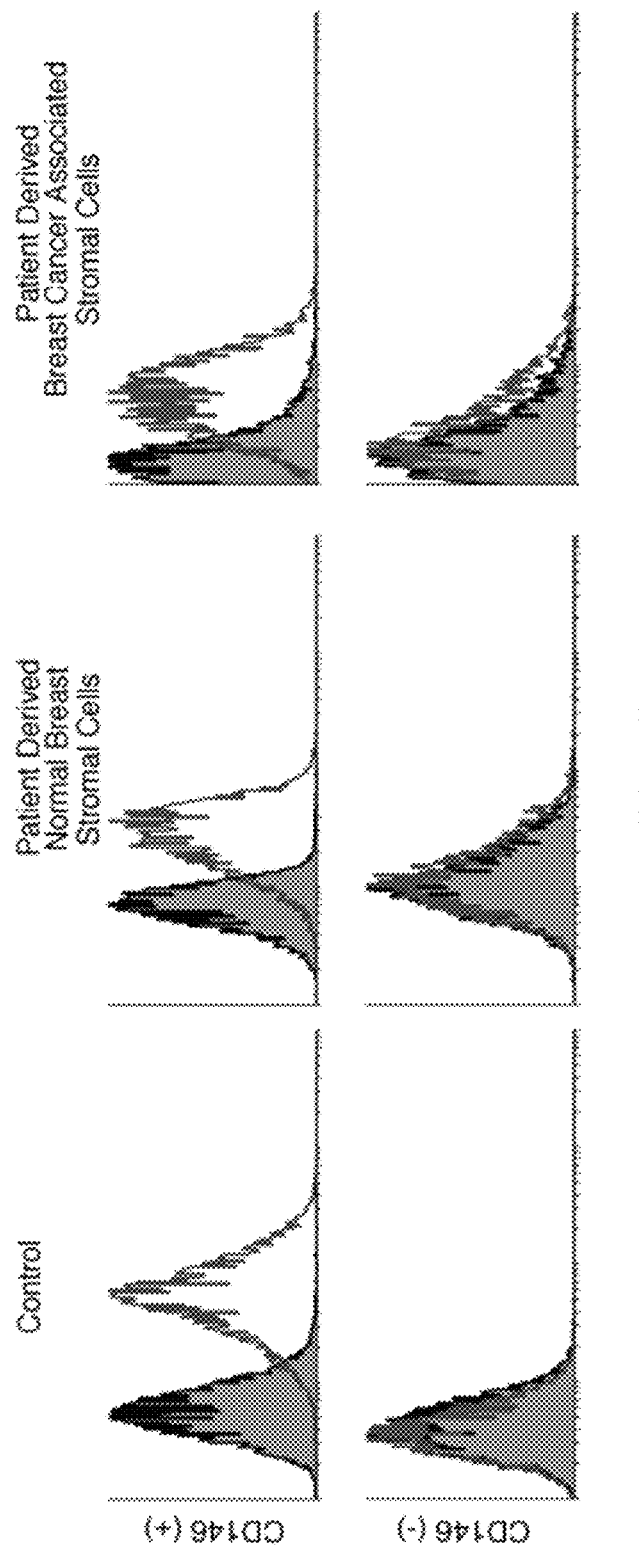
FIG. 1E is a set of six representative histograms demonstrating the presence of both $CD146^{pos}$ and $CD146^{neg}$ stroma in patient-derived normal and breast cancer associated tissue. N=14 patient tumor stroma samples and N=11 matched normal breast tissue samples.

Normal breast tissue was tested to determine if it contains $CD146^{pos}$ and $CD146^{neg}$ stromal subtypes. Primary human cancer-associated and normal breast stroma cells were isolated from 11 ER+ breast cancer patient samples, enriched for fibroblasts and primary cell lines were created using immortalization and clonal expansion. CD146 expression of individual clones was determined by flow cytometry. Indeed, based on the presence or absence of CD146, two cancer-associated fibroblast (CAF) subtypes in both normal breast and breast cancer-associated patient tissues were identified (FIG. 1E). Similar to the ER+ breast cancer tissue, both CAF subtypes were isolated from all 11 of the normal breast tissue samples analyzed. Taken together, these data demonstrate that the breast microenvironment is composed of at least two CAF subtypes, which can be identified according to CD146 expression and are common to both normal breast stroma and breast cancer-associated stroma. Patients with lower ER expression based on Allred scores (<8) have significantly decreased expression of $CD146^{pos}$ CAF compared to patients with high ER (Mired scores=8).

Example 3—$CD146^{pos}$ CAFs are Functionally and Phenotypically Akin to $CD146^{pos}$ Fibroblasts Found in Normal Bone Marrow The presence of CD146 CAF subtypes in normal and cancer associated breast tissue is similar to the dichotomy that exists in the microenvironment of normal bone marrow where $CD146^{pos}$ fibroblasts contribute to maintenance of the stem cell niche and $CD146^{neg}$ fibroblasts promote stem cell differentiation (Zuhrie S R and Wickramasinghe S N. *Leukemia Research.* 1991; 15(11):975-86). The differential contribution of both fibroblast subtypes in the bone marrow microenvironment is critical for healthy maintenance of the hematopoietic system. Therefore, we next determined if our breast CAF cell subtypes were similar to the $CD146^{pos}$ and $CD146^{neg}$ fibroblasts in normal bone marrow.

Figure 2A:
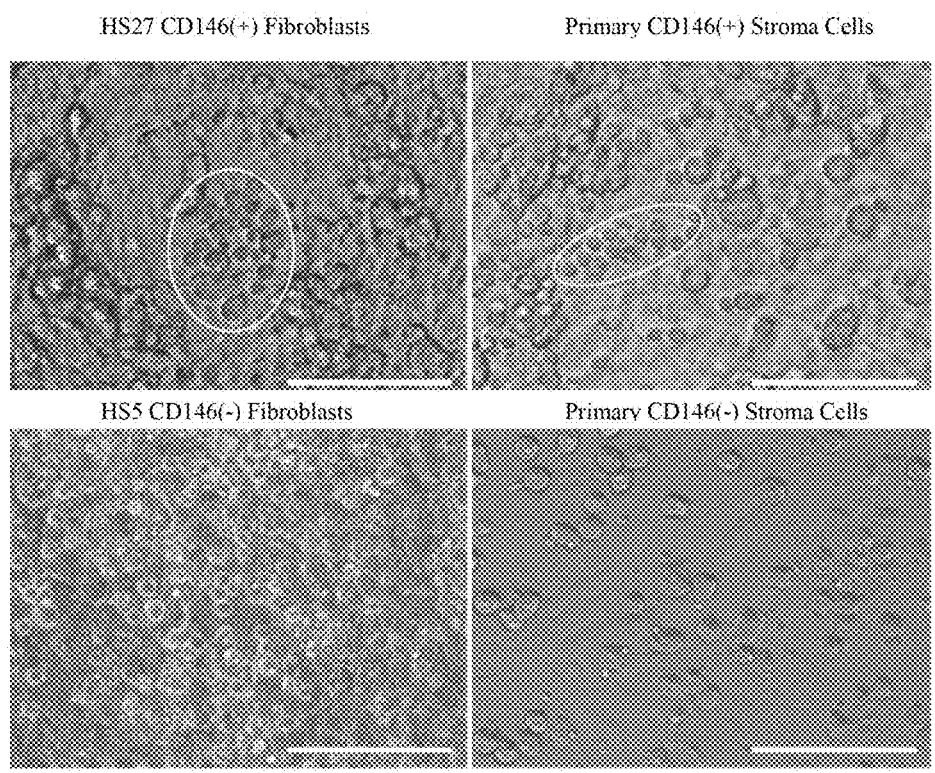
FIG. 2A is a set of four photographs reproduced in gray scale showing MNCs co-cultured with $CD146^{pos}$ fibroblasts (HS27a) or primary cancer associated stroma form significantly more cobblestone colonies (white circles) compared to CD146neg fibroblasts (HS5) or primary cancer associated stroma. Primary cancer derived stromal subtypes are functionally and genetically similar to normal bone marrow derived fibroblast subtypes HS27a (CD146+) and HS5 (CD146−) as shown in FIGS. 2A-2C. Scale bars: 20 µm. Cobblestone formation was quantified using 20× images. N=4 co-cultures per group. ****p<0.0001.
Figure 2B:
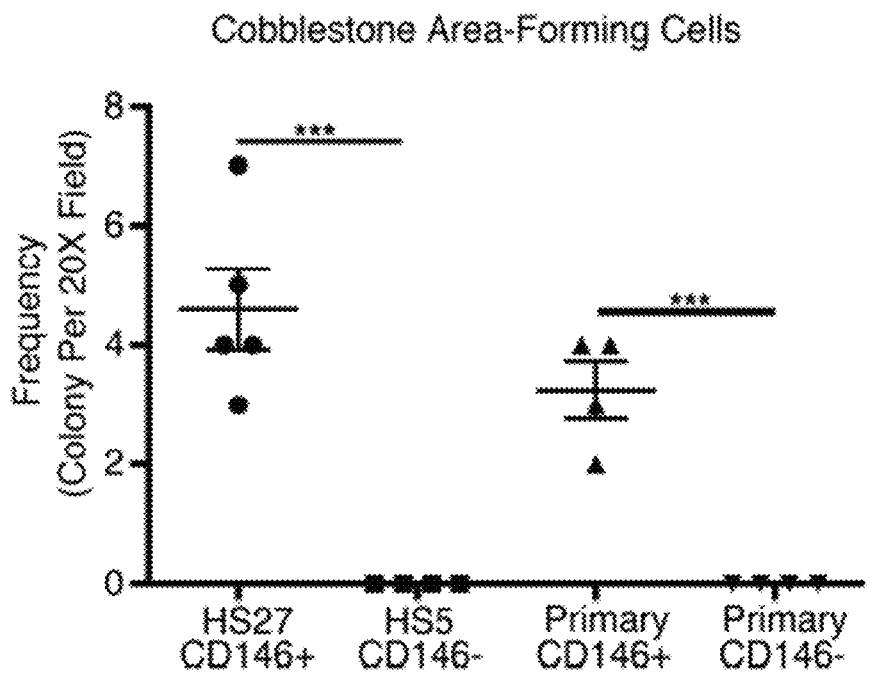
FIG. 2B is a graph illustrating the frequency of cobblestone area-forming cells in HS27a (CD146+) vs HS5 (CD146−) co-cultures and in primary CD146+ and CD146− tumor stroma co-cultures.

HS27a ($CD146^{pos}$) and HS5 ($CD146^{neg}$) fibroblast cell lines were derived from normal human bone marrow (Roecklein B A and Torok-Storb B. *Blood.* 1995; 85(4):997-1005). Because these cells originated from non-disease associated tissue, as opposed to cancer derived CAFs, HS27a and HS5 cells were used as representative of normal fibroblasts. In co-cultures with HS27a ($CD146^{pos}$) but not HS5 ($CD146^{neg}$) fibroblasts, mononuclear cells (MNCs) form colonies that are closely associated within the fibroblast layer. When viewed under phase contrast light microscopy the colonies resemble "cobblestones"; this assay is used as a functional readout of differences between fibroblast subtypes in normal bone marrow (Roecklein B A and Torok-Storb B. *Blood.* 1995; 85(4):997-1005). The cobble stone area forming cell (CAFC) assay was used to determine if the CAF subtypes that derived from human ER+ breast cancer tissue had similar functionality to the $CD146^{pos}$ and $CD146^{neg}$ bone marrow derived HS27a and HS5 fibroblasts, MNC/HS27a co-cultures had 5.8-fold more CAFC than MNC/HS5 co-cultures (FIGS. 2A and 2B). Similar to the results with the normal fibroblasts, MNCs co-cultured with CD146$^{pos}$ compared to CD146$^{neg}$ CAF cells had significantly more CAFC (3-fold greater) (FIGS. 2A and 2B). These results show that the CAFs promote equivalent MNC behavior as normal bone marrow-derived fibroblasts when stratified by CD146 expression.

Figure 2C:
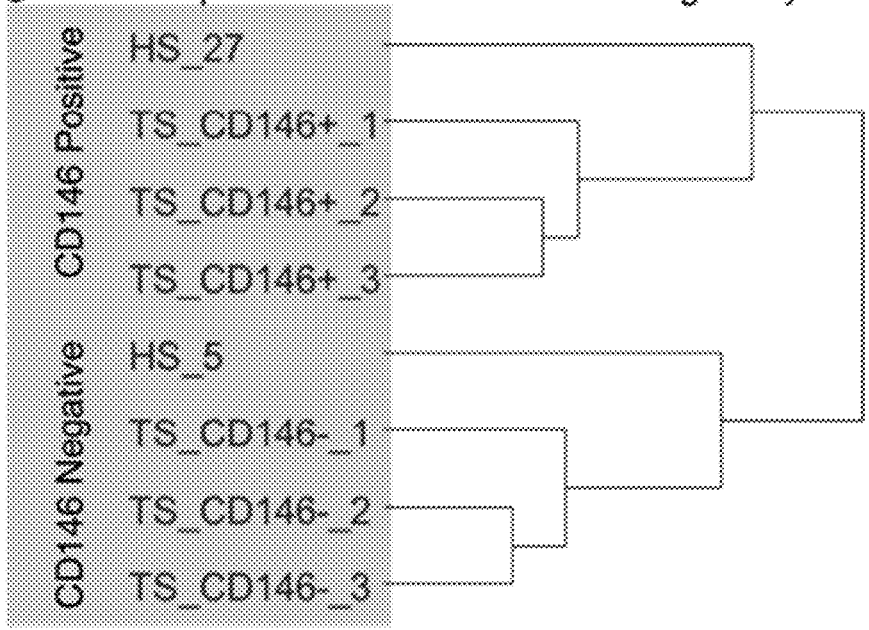
FIG. 2C is a graph showing gene expression hierarchical cluster analysis demonstrates that primary CD146+ tumor stroma is highly similar to normal HS27a fibroblasts and primary CD146− tumor stroma is similar to normal HS5 fibroblasts.

To determine if the CAF cells were phenotypically akin to HS27a and HS5 normal fibroblasts, gene expression signatures and hierarchical clustering analysis was employed. The gene expression signatures of CD146$^{neg}$ CAFs demonstrated significant similarity by clustering in the same family with normal HS5 fibroblasts (FIG. 2C). Likewise, CD146$^{pos}$ CAFs clustered with HS27 fibroblasts (FIG. 2C). The CAF cell lines have similar expression levels for genes associated with activated fibroblasts, including pro-collagen type 1 alpha, smooth muscle actin and fibroblast activation protein alpha (Table 1). These data support the assertion that the human cancer derived stromal subtypes have a fibroblast gene signature that is similar to the human bone marrow-derived HS27a and HS5 normal fibroblasts. Table 1 shows gene expression analysis in CD146$^{pos}$ (HS27a and our primary CAFs) and CD146$^{neg}$ (HS5 and our primary CAFs) demonstrates that all four cell types express high levels of genes associated with activated fibroblasts. Affymetrix gene analysis with a signal range of 0 to 13.

TABLE 1

Expression of genes associated with activated fibroblasts.

| Gene Symbol | CD146$^{pos}$ HS27a | CD146$^{pos}$ CAF | CD146$^{neg}$ HS27a | CD146$^{neg}$ CAF |
|---|---|---|---|---|
| ACTA2 | 11.3 | 12.3 | 7.9 | 11.8 |
| ASPN | 7.2 | 10.0 | 4.5 | 8.6 |
| COL1A1 | 13.2 | 13.2 | 12.7 | 13.0 |
| DES | 11.7 | 11.5 | 11.3 | 11.5 |
| FAP | 11.5 | 11.4 | 10.1 | 11.0 |
| OGN | 7.6 | 8.7 | 7.5 | 7.4 |
| PDGFRβ | 11.1 | 11.1 | 8.6 | 10.3 |
| PDPN | 7.7 | 7.3 | 8.5 | 6.9 |
| S100A4 | 9.6 | 10.5 | 9.7 | 9.6 |
| THY1 | 10.4 | 10.5 | 10.1 | 10.7 |
| VIM | 12.6 | 12.8 | 12.7 | 12.7 |
| ZEB1 | 9.4 | 10.9 | 10.0 | 10.4 |

Example 4—CD146 Expression in Fibroblasts Correlates with Patient Outcomes

The gene signature from the stromal component of breast cancer patients accurately identifies normal versus cancer tissue and predicts patient outcomes (Finak G., et al, Stromal gene expression predicts clinical outcome in breast cancer. Nature Medicine. 2008; 14(5):518-27) Fibroblast subtype composition of breast cancer patient tissue was examined to see if it would be sufficient to predict outcome. To test this, the gene signatures of HS27a, HS5, CD146$^{pos}$ CAFs and CD146$^{neg}$ CAFs were compared to published gene expression data of normal and breast cancer-associated stroma. Considerable overlap of expressed annotated genes was verified in all four cell types (HS27a, HS5, CD146$^{pos}$ and CD146$^{neg}$) with the gene set used to identify breast stromal origin and to generate predictions of breast cancer patient outcomes (128 of the 163 stromal genes identified by Finak et. al). The 128 identified stromal genes in the data set were used to determine if CD146$^{pos}$ or CD146$^{neg}$ fibroblasts clustered with normal breast stroma or breast cancer-associated stroma in the published data set. Because HS5 cells and the CD146neg CAFs cluster in a single family, and HS27a cells cluster with the CD146$^{pos}$ CAFs, cells were pooled from each subtype together for the comparison. The gene expression profile from HS5 (CD146$^{neg}$) fibroblasts and the breast cancer patient-derived CD146$^{neg}$ CAFs aligned with the Finak et. al, gene profile pattern for breast cancer associated stroma, whereas a CD146$^{pos}$ gene profile from HS27a or our CD146$^{pos}$ CAFs aligned with normal breast associated stroma (FIG. 3). Furthermore, CD146$^{neg}$ CAFs predicted poor/mixed clinical outcomes for patients with ER+ breast cancer compared to CD146$^{pos}$ CAFs, which were aligned with good clinical outcomes.

Taken together, these data demonstrate that CD146 expression is a distinguishing characteristic of stromal fibroblasts in the normal and diseased breast that mimics the fibroblast hierarchy present in the hematopoetic system, demarcates normal vs. tumor-associated stroma, and is predictive of disease outcomes.

Figure 4A:
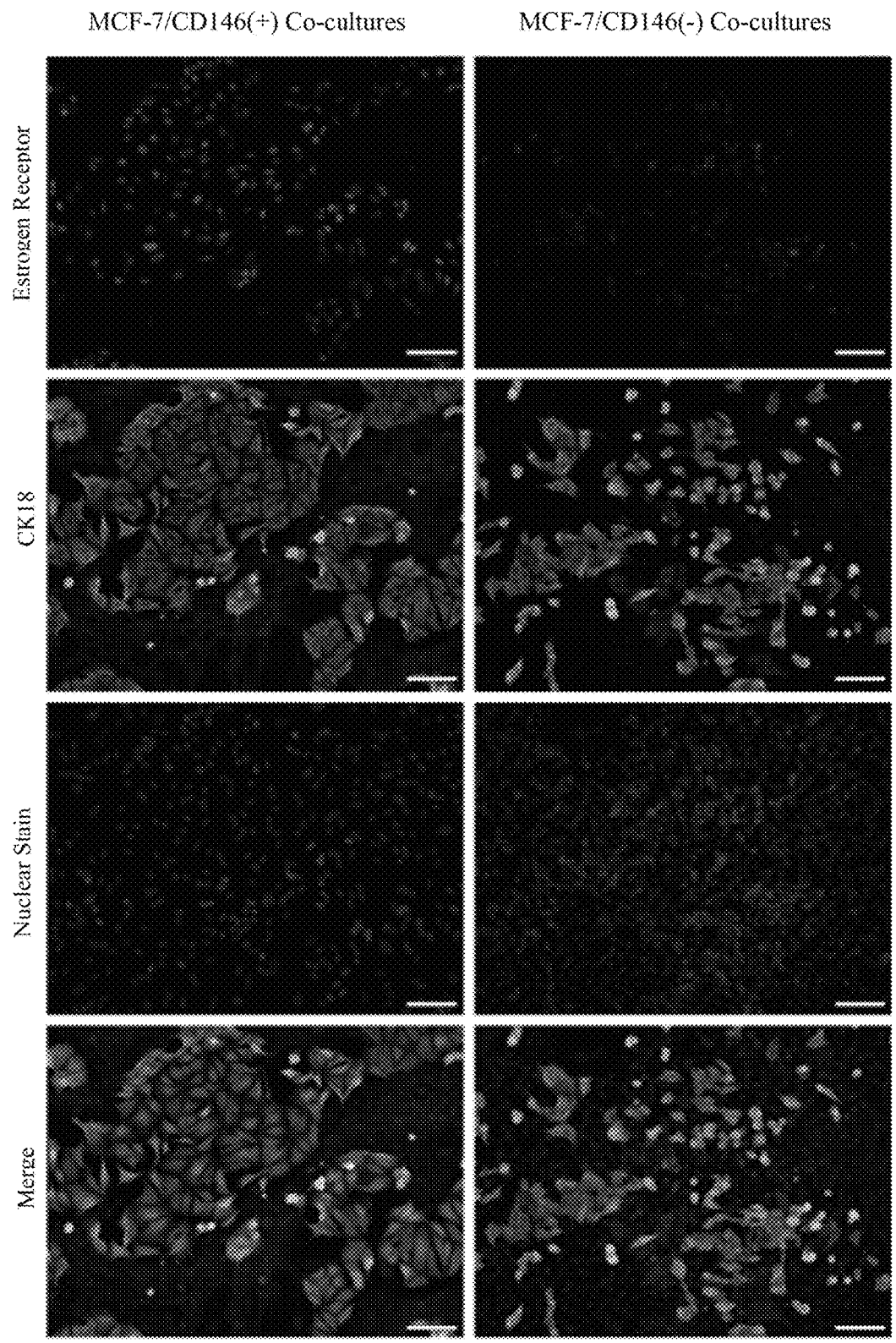
FIG. 4A is a set of eight photographs showing representative immunofluorescence staining for ER (upper two images) and the tumor cell maker CK18 (two images immediately below the images staining for ER) in co-cultures of MCF-7 cells with HS27a ($CD146^{pos}$ left panel of photographs) or HS5 ($CD146^{neg}$ right panel of photographs) fibroblasts showing decreased ER expression in $CD146^{neg}$ co-cultures compared to $CD146^{pos}$ co-cultures. $CD146^{pos}$ CAFs sustains ER expression in ER+ breast cancer cells, whereas $CD146^{neg}$ CAFs promote decreased ER expression as shown in FIGS. 4A-4D. Scale bars: 20 µm.
Figure 4B:
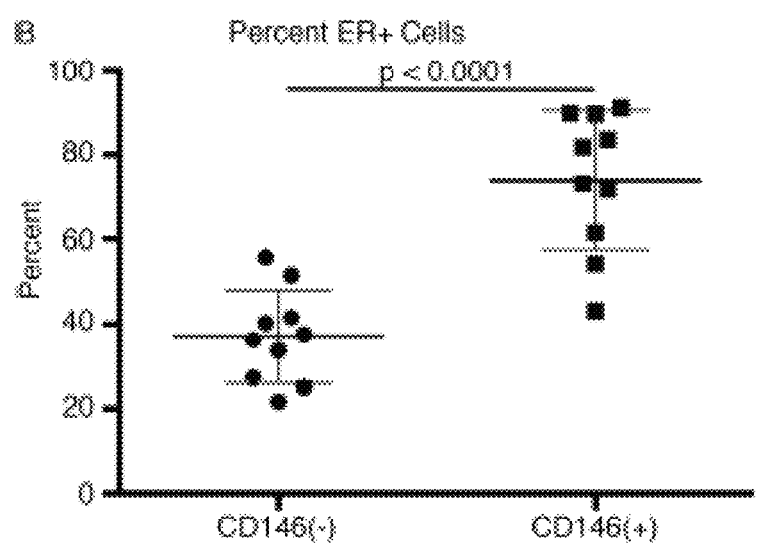
FIG. 4B is a graph illustrating the analysis of 4 replicates imaged in 3 positions and quantified for the percent of ER positive tumor cells and demonstrates a significant reduction in ER expression in co-cultures with $CD146^{neg}$ fibroblasts.
Figure 7:
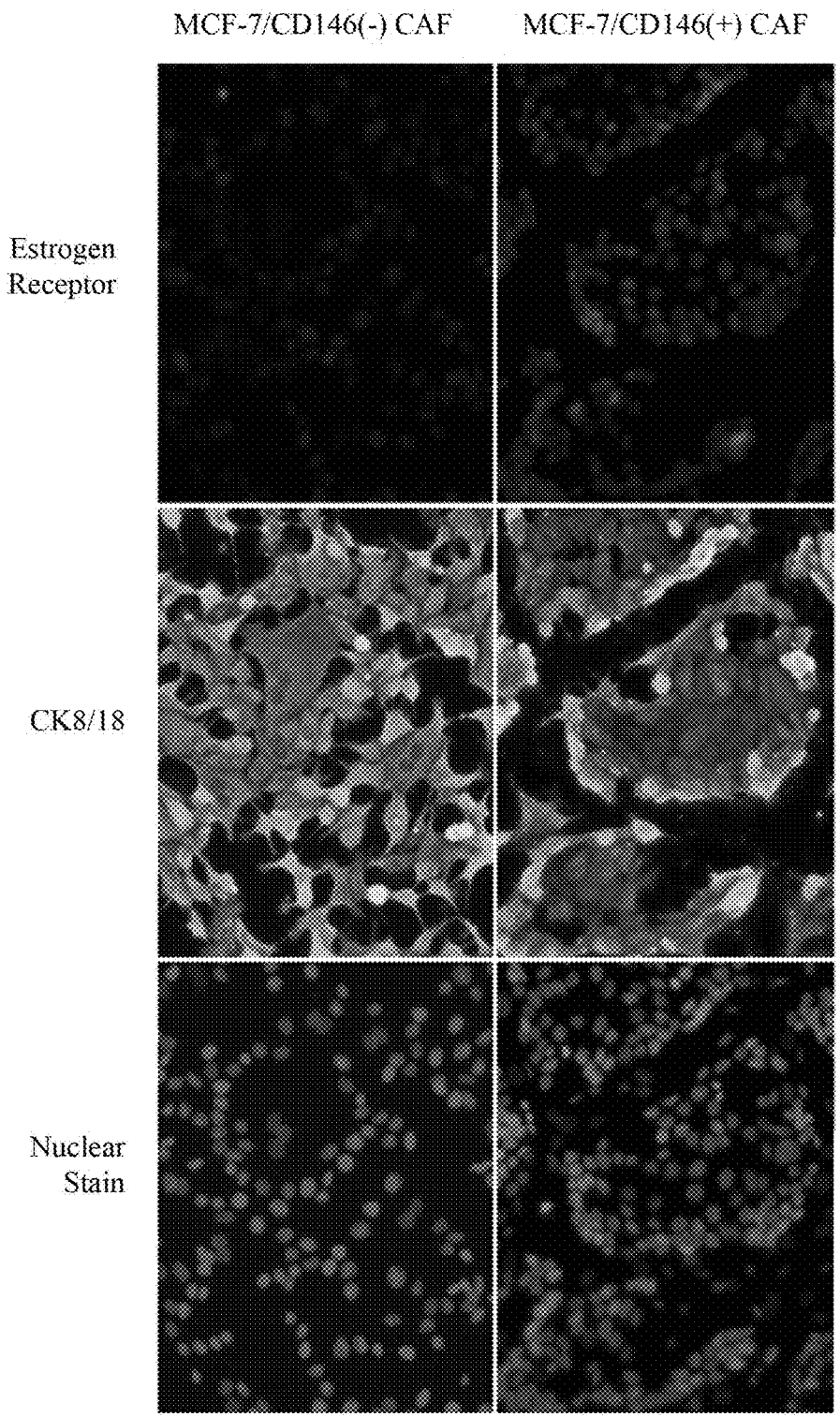
FIG. 7 is a set of six photographs illustrating that CD146$^{pos}$ CAFs sustains ER expression in ER+ breast cancer cells, whereas CD146$^{neg}$ CAFs promote decreased ER expression. MCF-7 cells were mixed with the primary derived CAF fibroblasts and tumors were established in NSG mice and harvested for immunofluorescence staining for ER (red/light gray in gray scale) and CK18 (green/light gray in gray scale) showing decreased ER expression in tumors mixed with our primary CD146$^{neg}$ CAFs compared to those mixed with CD146$^{pos}$ fibroblasts.

Example 5—CAF Subtypes Differentially Influence ER Expression in Breast Cancer Cells To pursue a functional role for CAFs in distinguishing tumor characteristics, the phenotype and growth of ER+ breast cancer cells (BCCs) grown in conjunction with the fibroblast subtypes was compared. ER+ MCF-7 BCCs were co-cultured with CD146$^{pos}$ and CD146$^{neg}$ fibroblasts in estrogen depleted media for 120 hours and stained for ER using immunofluorescence (FIG. 4A). Cytokeratin 18 (CK18) was used to positively identify tumor cells. ER expression was higher in MCF-7 cells when they were co-cultured with CD146$^{pos}$ fibroblasts (74% vs 37% ER+ cells, FIG. 4B). Similar results were observed when BCCs were co-cultured with the primary CAF subtypes (FIG. 7).

Figure 4C:
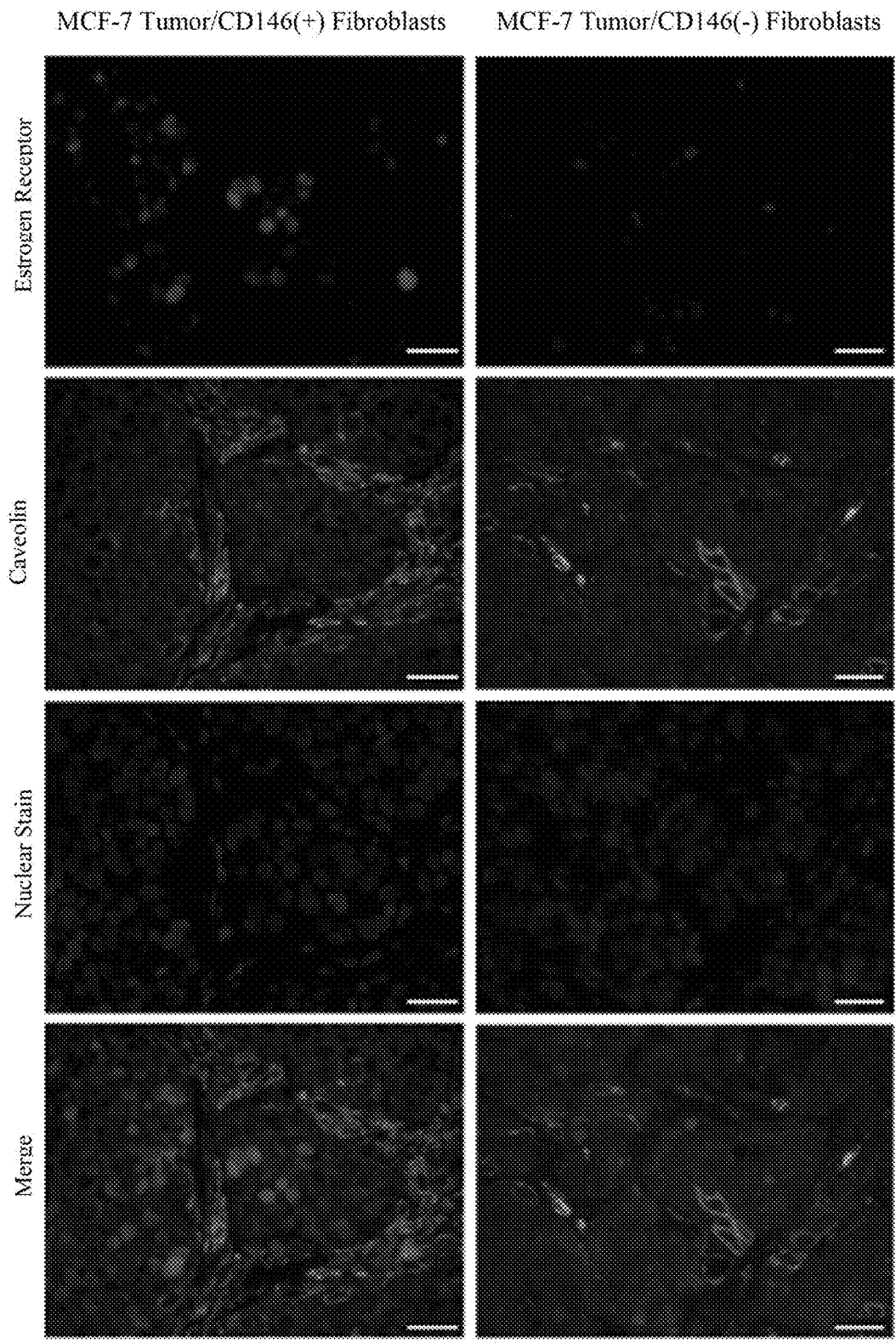
FIG. 4C is a set of eight photographs showing that mixed MCF-7/fibroblast (HS27a or HS5) tumors that were established in NSG mice and harvested for immunofluorescence staining for ER (upper two images) and CK18 (two images immediately below the images staining for showing decreased ER expression in tumors mixed with $CD146^{neg}$ fibroblasts. Scale bars: 20 µm.
Figure 4D:
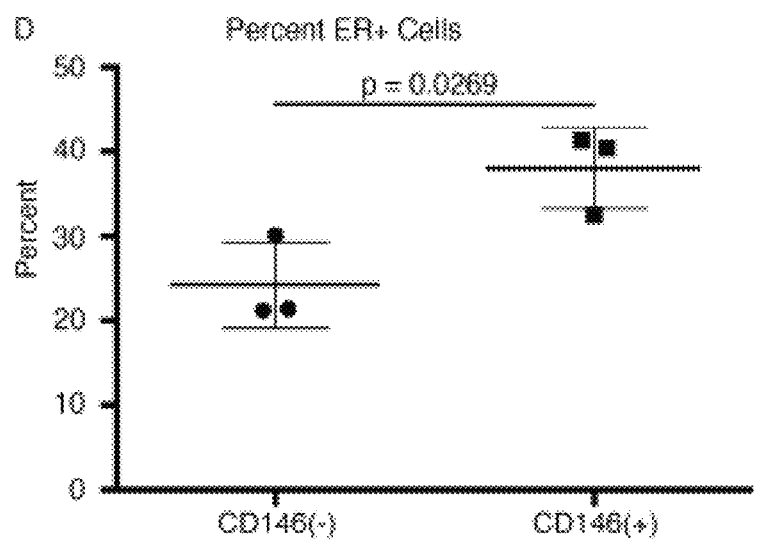
FIG. 4D is a graph illustrating the analysis of 3 animals per group, imaged in 1 position and quantified for the percent of ER positive tumor cells demonstrates a significant reduction in ER expression in tumors mixed with $CD146^{neg}$ fibroblasts.

To assess if CAF subtypes would affect ER in tumors similarly, ER+ MCF-7 cells co-implanted with the fibroblast subtypes were grown as xenografts. A 1:1 mixture of MCF-7 cells was injected with CD146$^{pos}$ or CD146$^{neg}$ fibroblasts. Tumors were established and allowed to grow with estrogen supplementation for 36 days prior to collection. Tumor size was not significantly different between fibroblast subtypes. Xenograft tumors were co-stained with ER plus caveolin to identify the fibroblasts. MCF-7 xenograft tumors mixed with CD146$^{pos}$ fibroblasts expressed higher levels of ER (FIG. 4C) compared to MCF-7/CD146$^{neg}$ mixed tumors (38% vs 24%, FIG. 4D), These data show that CD146$^{neg}$ fibroblasts drive decreased ER expression in BCCs and suggest a mechanism for stroma-induced development of anti-endocrine resistance.

Figure 5A:
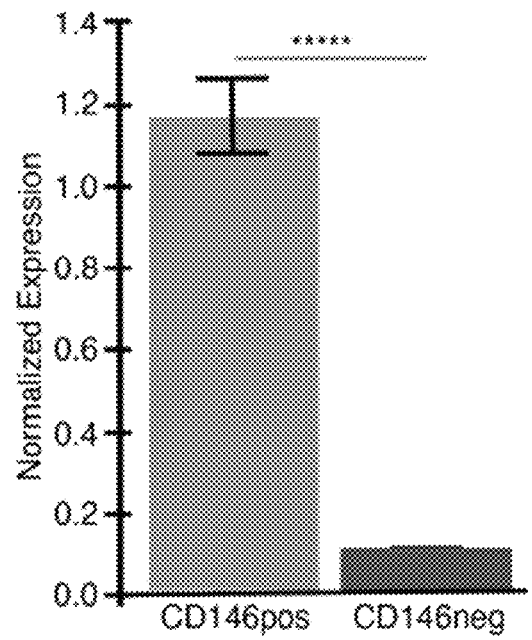
FIG. 5A is a graph illustrating ER transcription in MCF7 cells. MCF7 cells cultured for 5 days in conditioned media from $CD146^{pos}$ (HS27a) fibroblasts have significantly more ER gene expression than MCF-7 cells grown in conditioned media from $CD146^{neg}$ (HS5) fibroblasts. Influence of $CD146^{neg}$ CAFs programs ER+ breast cancer cells to bypass estrogen dependent proliferation through EGFR and decreases tamoxifen sensitivity as shown in FIGS. 5A-5D. (*p<0.001; **p<0.0001.)
Figure 5B:
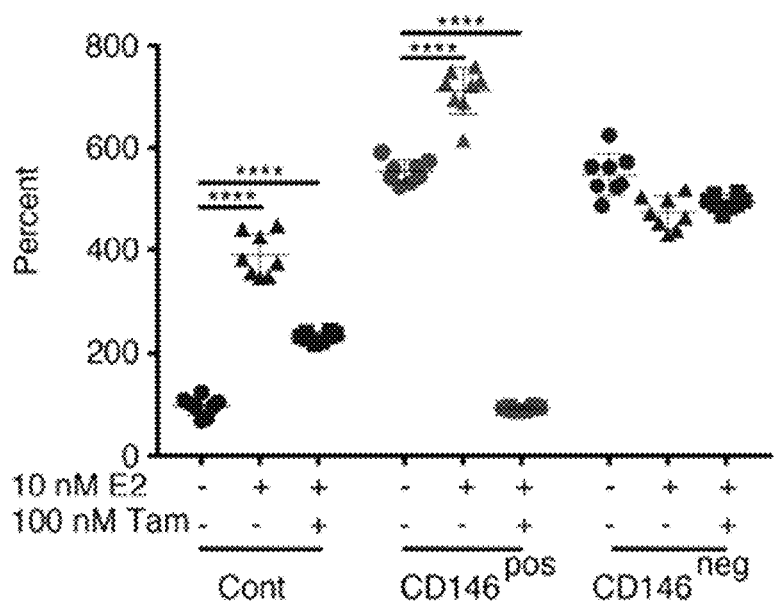
FIG. 5B is a graph illustrating MCF7 proliferation assays. SRB total protein analysis of MCF-7 cells cultured in conditioned media from $CD146^{pos}$ (HS27a) fibroblasts have significantly increased proliferation in response to estrogen treatment and significantly decreased proliferation in response to treatment with 4-OH-tamoxifen. In contrast, conditioned media from $CD146^{neg}$ fibroblasts renders MCF-7 cells unresponsive to estrogen and 4-OH-tamoxifen treatment. (*p<0.001; **p<0.0001.)
Figure 8:
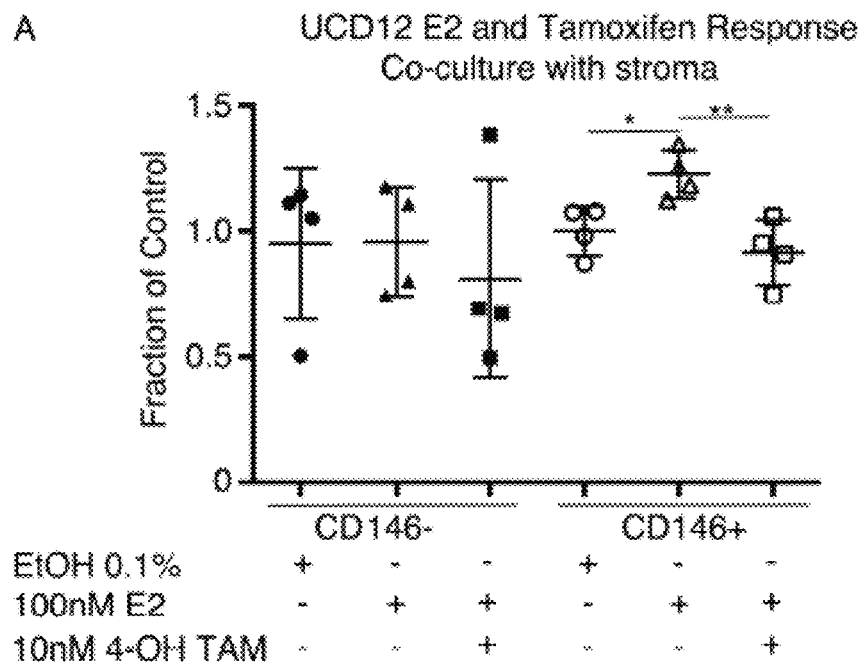
FIG. 8 is a pair of graphs showing the influence of CD146$^{pos}$ CAFs which program ER+ breast cancer cells to proliferate in response to estrogen and to respond to tamoxifen treatment. (A) UCD12 cells are ER+ primary tumor cells generated at the University of Colorado from a patient derived tissue. Live cell imaging of UCD12/CAF co-cultures demonstrate that CD146$^{pos}$ fibroblasts promote UCD12 proliferation in response to estrogen treatment and decreased proliferation in response to tamoxifen treatment as measured by live cell imaging. In contrast, influence from CD146$^{neg}$ fibroblasts results in loss of estrogen and tamoxifen responsiveness. (B) SRB total protein analysis in ER+ T47D cells measuring proliferation demonstrates that influence from CD146$^{pos}$ conditioned media renders T47D cells estrogen and tamoxifen responsive, whereas influence from CD146$^{neg}$ conditioned media redners them unresponsive. *p<0.05; p<0.01; **p<0.0001.
Figure 8:
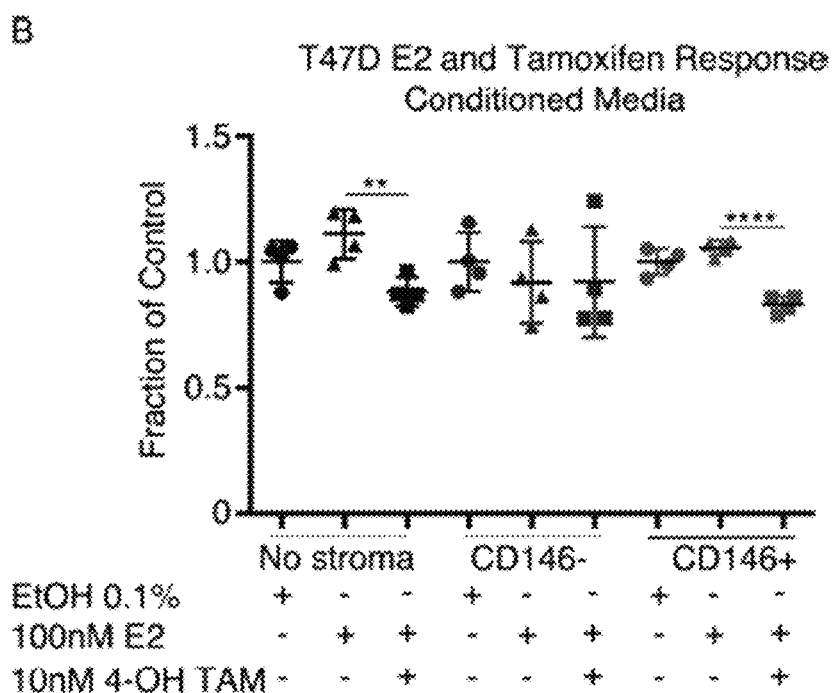

Example 6—ER+ Breast Cancer Cells Use ER Growth Dependent Pathways when Stimulated by CD146$^{pos}$ Fibroblasts ER+ breast cancer cells utilize estrogen as a mitogen, rendering anti-endocrine therapy an effective initial treatment for ER+ breast cancer patients. To determine if CD146$^{pos/neg}$ fibroblasts influenced estrogen dependent proliferation in ER+ breast cancer cells, co-culture and conditioned media experiments were used. Proliferation rates were analyzed using the total protein SRB assay or live cell imaging using Incucyte Zoom (Essen BioScience, Ann Arbor, Mich.). MCF-7 cell cultures were grown in E2-starved conditions for 72 hours prior to treatment with conditioned media (CM). RT-PCR analysis verified that loss of ER expression was obtainable simply by treating MCF-7 cells with conditioned media from CD146$^{neg}$ fibroblasts (FIG. 5A). In vehicle treated samples after 72 hours, conditioned media from both CD146$^{pos}$ and CD146$^{neg}$ fibroblasts increased. MCF-7 BCC proliferation 5-fold (FIG. 5B). Treatment with estrogen (17β-estradiol) significantly increased proliferation of BCCs grown in unconditioned or CD146$^{pos}$ CM (2.9-fold and 1.3-fold respectively) (FIG. 5B). In contrast, estrogen did not alter proliferation of BCCs treated with CD146$^{neg}$ CM (FIG. 5B). Tamoxifen significantly inhibited estrogen-induced proliferation of BCCs in unconditioned or CD146$^{pos}$ fibroblasts CM by over 7-fold (FIG. 5B). However, proliferation of BCCs with CD146$^{neg}$ fibroblast CM was not significantly changed with tamoxifen (FIG. 5B). Similar results were obtained using co-cultures of MCF-7 with fibroblasts instead of CM, and with two other ER+ BCCs, UCD12 (FIG. 8A) and T47D (FIG. 8B). These data demonstrate that ER+ BCCs influenced by CD146$^{pos}$ fibroblasts remain estrogen responsive and anti-estrogen sensitive; however, influence from CD146$^{neg}$ fibroblasts renders ER+ BCCs estrogen unresponsive and tamoxifen insensitive.

Figure 5C:
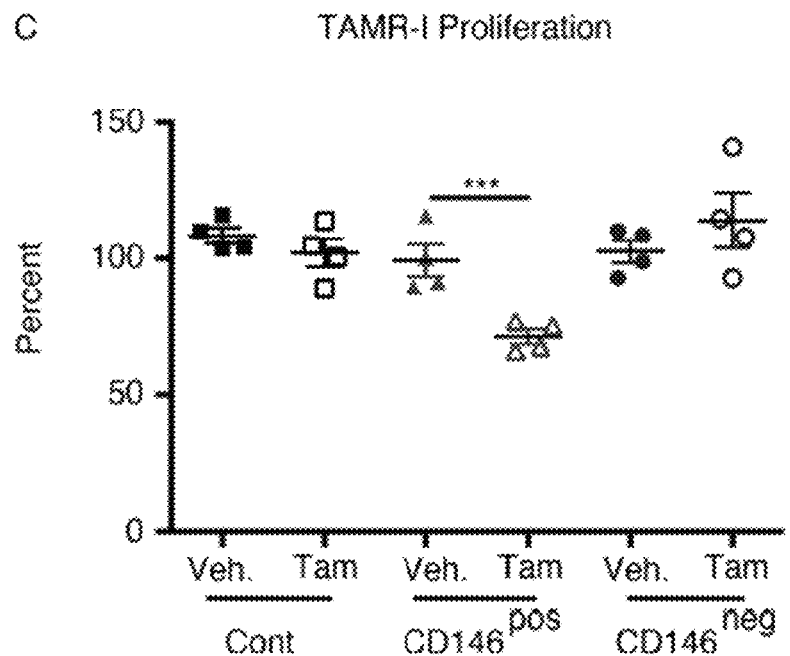
FIG. 5C is a graph illustrating TAMR-I proliferation assays. SRB total protein analysis of tamoxifen resistant TAMR-I cells cultured in conditioned media from CD146$^{pos}$ (HS27a) fibroblasts have significantly decreased proliferation when treated with 4-OH-tamoxifen. (*p<0.001; **p<0.0001.)

The data presented herein indicates that CD146 fibroblast subtypes influence BCC response to tamoxifen. The response of tamoxifen resistant MCF-7/TAMR-1 (TAMR-1) cells to tamoxifen when grown under the influence of CD146$^{pos}$ or CD146$^{neg}$ fibroblasts was tested as a corollary. TAMR-1 cells are a tamoxifen resistant derivative of MCF-7 BCCs (Cittelly D M, et al., Mol Cancer, 2010; 9(317)). TAMR-1 cells were cultured in unconditioned or conditioned media from CD146$^{pos}$ or CD146$^{neg}$ fibroblasts and treated with 10 nM estrogen alone or with 100 nM 4-hydroxy-tamoxifen (Tamoxifen). Tamoxifen treatment had no effect on proliferation of BCCs in unconditioned or CD146$^{neg}$ fibroblasts CM (FIG. 5C). However, TAMR-1 cells cultured in CD146$^{pos}$ fibroblast CM had significantly decreased proliferation with tamoxifen (29% compared to control) (FIG. 5C), suggesting TAMR-1 cells gained sensitivity to tamoxifen. These data show that fibroblast subtypes can influence tamoxifen sensitivity of ER+ BCCs.

Example 7—ER+ Breast Cancer Cells Use EGFR Growth Dependent Pathways when Stimulated by CD146$^{neg}$ Fibroblasts The development of endocrine resistance appears to involve cross-talk between ER and the EGFR/HER2 pathway (Nicholson, R I, et al., Endocr Relat Cancer. 2001; 8(3):175-82). GFP-labeled MCF-7 or TAMR-1 tumor cells were co-cultured with unlabeled. CD146$^{pos}$ or CD146$^{neg}$ fibroblasts in estrogen depleted media. After five days of culture the fibroblasts were separated from the tumor cells by flow sorting and prepared for RNAseq analysis. Metacore pathway analysis of the gene expression data shows that both MCF-7 and TAMR-1 cells co-cultured with CD146$^{neg}$ fibroblasts are enriched for EGFR pathway proteins compared to co-cultures with CD146$^{pos}$ fibroblasts (p=2.140e−11 and 1.945e−13 respectively). In fact, using pre-generated Metacore Pathway Maps, the data demonstrate that MCF-7 and TAMR-1 cells influenced by CD146$^{neg}$ fibroblasts have increased expression for EGFR related genes, whereas MCF-7 and TAMR-1 cells influenced by CD146$^{pos}$ fibroblasts have increased expression for ER-related genes.

Figure 5D:
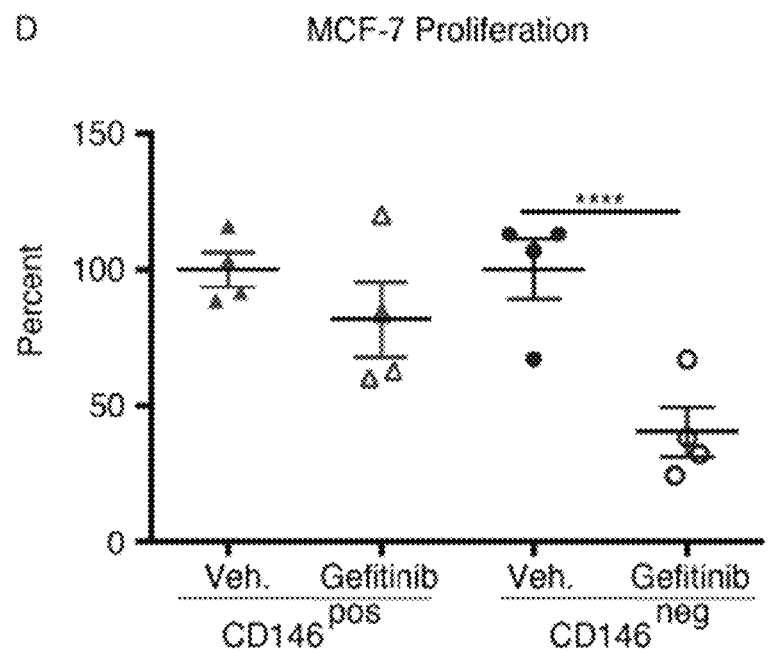
FIG. 5D is a graph illustrating MCF7 proliferation assays. Live cell imaging and quantification of MCF-7 proliferation in response to the specific EGFR inhibitor gefitinib demonstrates that CD146$^{neg}$ fibroblasts induce significantly decreased proliferation in MCF-7 cells, whereas proliferation of MCF-7 cells co-cultured with CD146$^{pos}$ (HS27a) fibroblasts is not significantly changed. (*p<0.001; **p<0.0001.)

As a corollary, it was determined if growth of BCCs influenced by CD146$^{neg}$ fibroblasts were sensitive to EGFR inhibition. GFP labeled MCF-7 BCCs were co-cultured with CD146$^{pos}$ or CD146$^{neg}$ fibroblasts in serum reduced media (2.5% FBS) for 48 hours and then treated the cells with the EGFR specific inhibitor gefitinib (10 μM). Proliferation was reduced by 60% in BCCs cultured with CD146$^{neg}$ fibroblasts by 72 hours post-treatment with gefitinib (FIG. 5D). Proliferation was unchanged for MCF-7 cells cultured with CM from CD146$^{pos}$ and treated with gefitinib. The data suggests that BCCs influenced by CD146$^{neg}$ but not CD146$^{pos}$ fibroblasts have increased dependency on EGFR-mediated proliferation.

Figure 6A:
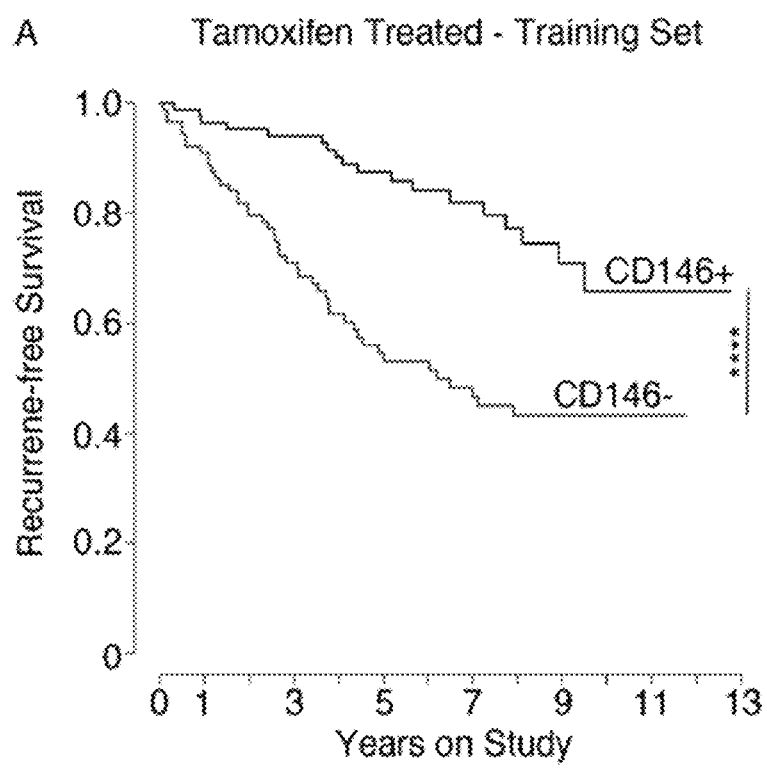
FIG. 6A is a graph illustrating the tamoxifen treated training set. Patient training set for a gene signature consisting of 5 genes (PRKCA, MACROD2, SMARCA4, BNIP3, MYO1B) predicted to be up and 4 genes (RPLP1, CDC42EP4, MAP2K4 and SIAH2) predicted to be down in the epithelial component of ER+ breast cancer was generated from RNAseq data in MCF-7/CAF co-cultures.
Figure 6B:
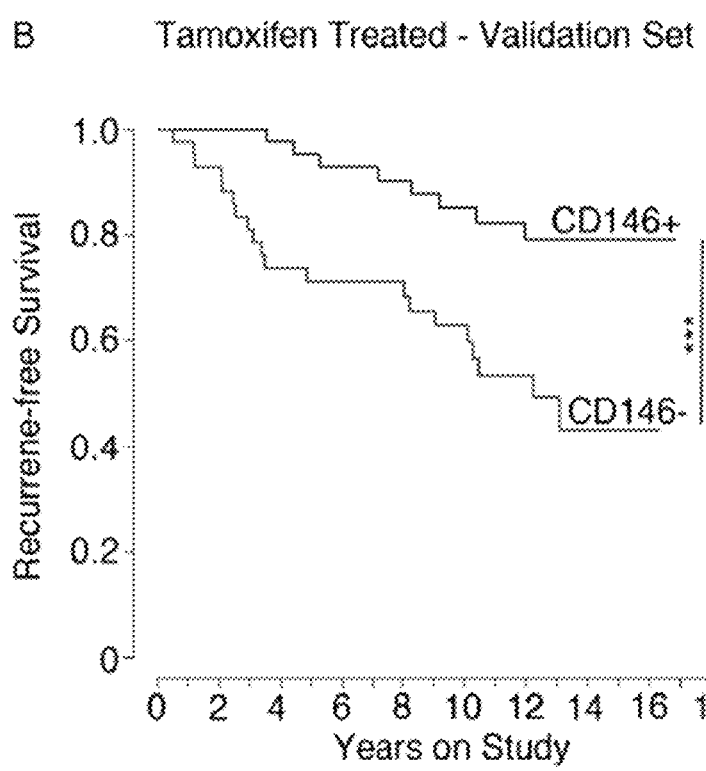
Figure 6C:
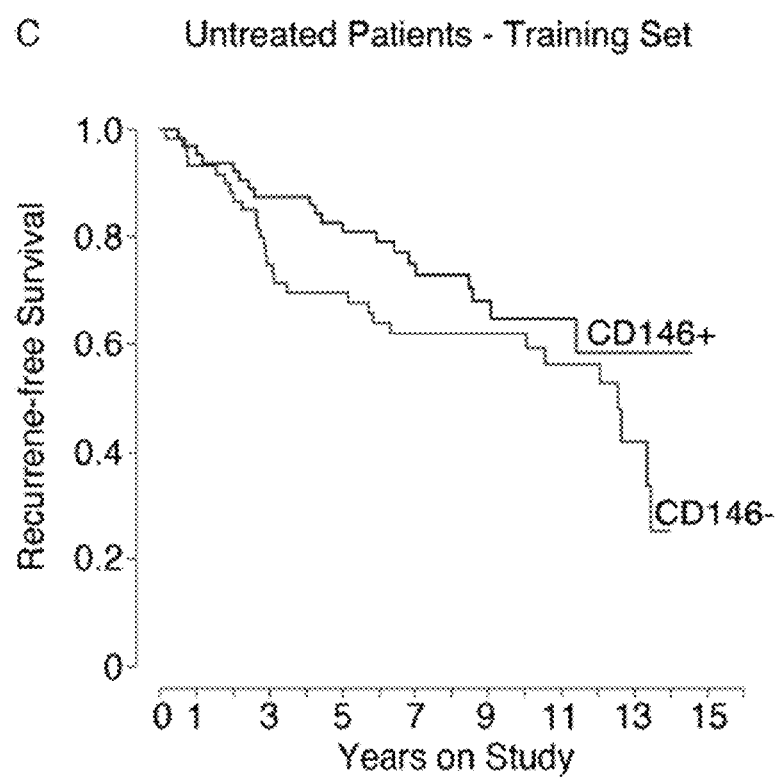
Figure 6D:
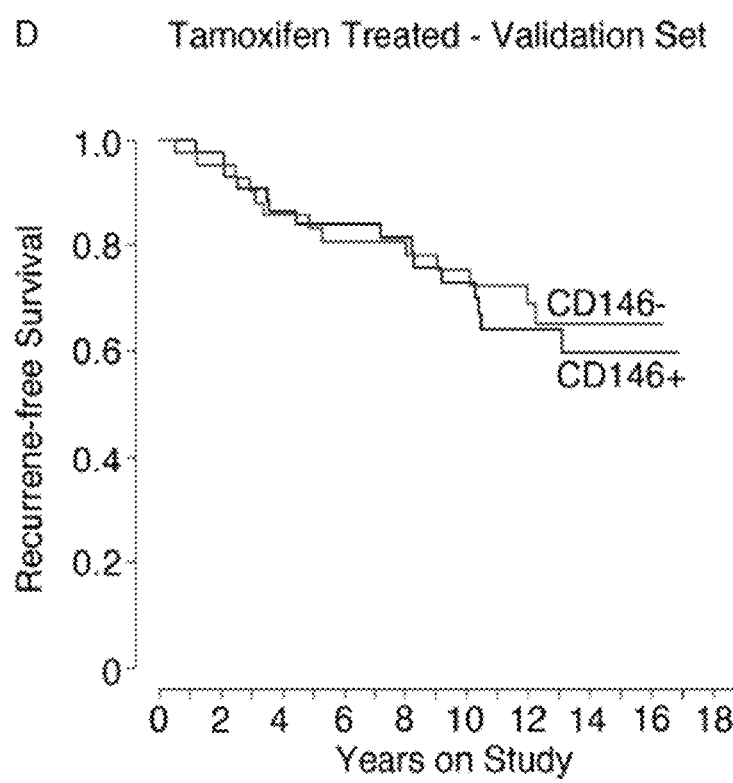

Example 8—CAF Induced Gene Expression Signature Predicts Breast Cancer Recurrence in Patients Treated with Tamoxifen To determine gene expression changes that occur in BCCs with fibroblast subtypes MCF-7 cells were co-cultured with CD146$^{pos}$ and CD146$^{neg}$ fibroblasts and RNA-seq was used to identify relative changes in gene expression between the two groups. Analysis revealed that MCF-7 cells co-cultured with CD146$^{neg}$ vs. CD146$^{pos}$ fibroblasts had increased expression of transcripts from 21 genes identified in the literature as upregulated in tamoxifen resistance (Huber-Keener K J, et al., PloS one 2012; 7(17):e41333; De Placido S, et al., Clinical cancer research, an official journal of the American Association for Cancer Research. 2003:9(3)1039-46; Jansen M P, et al., Journal of clinical oncology: official journal of the American Society of Clinical Oncology, 2005; 23(4):732-40; Kalyuga M, et al., PLoS Biol. 2012; 10(12): e1001461; Mosheni M, et al., PNAS. 2014; 111(49):17606-11; Oosterkamp H M, et al, Cancer research. 2014; 74(14): 3810-20; Elias D, et al., Oncogene. 2015; 34(15):1919-27. (Table 2—RNAseq analysis of MCF-7 cells after co-culture with CD146$^{pos}$ (HS27a) fibroblasts reveals increased expression of genes identified in literature to be associated with tamoxifen responsiveness in ER+ breast cancer, as compared to expression in MCF-7 cells co-cultured with CD146$^{neg}$ (HS5) fibroblasts. Genes in bold/underline are included in the gene signature that were developed as predictive for recurrence-free survival). Conversely, MCF-7 cells co-cultured with CD146$^{pos}$ vs. CD146$^{neg}$ fibroblasts had increased expression of 15 genes identified in the literature as down-regulated in tamoxifen resistance (Stable 3—RNAseq analysis of MCF-7 cells after co-culture with CD146$^{neg}$ (HS5) fibroblasts reveals increased expression of genes identified in literature to be associated with tamoxifen resistance in ER+ breast cancer, as compared to expression in MCF-7 cells co-cultured with CD146$^{pos}$ (HS27a) fibroblasts. Genes in bold/underline are included in the gene signature that was developed as predictive for recurrence-free survival). From these lists a set of 9 genes was identified (5 up-regulated genes in MCF-7/CD146$^{neg}$ cells and 4 genes up-regulated in MCF-7/CD146$^{pos}$ cells) that produced a high confidence gene signature that can reliably predict recurrence-free survival in patients treated with tamoxifen (training set 181 patients p=3×10$^{-5}$ and validation set 87 patients p=0.00147) (FIG. 6A-B). Importantly, the 9-gene set was not predictive of recurrence-free survival in a set of 125 patients that were not treated with tamoxifen, suggesting that it is linked to tamoxifen resistance and not merely associated with poor patient prognosis (FIG. 6C). Finally, a signature composed of all 36 genes is not predictive (FIG. 6D). Taken together, these data show that influence from CD146$^{pos}$ fibroblasts is predictive of improved recurrence free survival after tamoxifen treatment, whereas influence from CD146$^{neg}$ fibroblasts produces a tumor gene signature predictive of poorer prognosis in tamoxifen treated breast cancer patients.

TABLE 2

Tamoxifen responsive genes up-regulated in ER+ breast cancer cells influenced by CD146$^{pos}$ fibroblasts.

| Gene Symbol | RefSeq | MCF7_CD146− | MCF7_CD146+ |
|---|---|---|---|
| FYN | NM_153048 | 3.71338 | 0.0498162 |
| PRKCA | NM_002737 | 2.05126 | 0.041475 |
| GBP1 | NM_002053 | 2.97616 | 0 |
| PRLR | NM_001204315 | 12.9416 | 0 |
| LYN | NM_001111097 | 4.45319 | 0 |
| ANKRD32 | NM_032290 | 13.8243 | 0 |
| INTS12 | NM_001142471 | 14.6722 | 0 |
| TATDN1 | NM_032026 | 18.691 | 0 |
| ELF5 | NM_001243080 | 8.58448 | 0 |
| RAB27B | NM_004163 | 9.03404 | 0 |
| MACROD2 | NM_080676 | 2.06923 | 0.0368517 |
| API5 | NM_006595 | 20.9138 | 0 |
| TIMP3 | NM_000362 | 22.5946 | 18.6913 |
| FN1 | NM_002026 | 26.5461 | 0.329774 |
| TNC | NM_002160 | 4.53082 | 2.26048 |
| SMARCA4 | NM_001128849 | 4.30675 | 0 |
| BNIP3 | NM_004052 | 94.2657 | 72.2238 |
| MYO1B | NM_001161819 | 27.1939 | 20.1926 |
| NPM1 | NM_001037738 | 100.011 | 32.5057 |
| CAMTA1 | NM_001242701 | 3.00467 | 0 |
| PSAP | NM_002778 | 270.312 | 17.68844 |

TABLE 3

Tamoxifen resistant genes up-regulated in ER+ breast cancer cells influenced fibroblasts by CD146$^{neg}$

| Gene Symbol | RefSeq | MCF7_CD146− | MCF7_CD146+ |
|---|---|---|---|
| RPLP1 | NM_001003 | 2848.97 | 3208.43 |
| USP9X | NM_001039591 | 7.5691 | 16.1008 |
| FAM8A1 | NM_016255 | 2.75613 | 4.67271 |
| APPBP2 | NM_001282476 | 0 | 52.4936 |
| INPPL1 | NM_001567 | 18.5688 | 21.4406 |
| DBR1 | NM_016216 | 3.36696 | 11.4302 |
| TXN2 | NM_012473 | 35.4597 | 71.8815 |
| SERPINB1 | NM_073112 | 21.6986 | 34.176 |
| PRPSAP2 | NM_001243941 | 0.000529618 | 27.5369 |
| CDC42EP4 | NM_012121 | 8.87546 | 9.11989 |
| MAP2K4 | NM_003010 | 7.99873 | 14.5411 |
| IL4R | NM_001257997 | 3.83766 | 5.63966 |
| PSME1 | NM_001281529 | 19.4186 | 92.9464 |
| SIAH2 | NM_005067 | 22.0281 | 32.0894 |
| MST4 | NM_001042452 | 26.0504 | 36.1343 |

Example 9—Prevention of Metastatic Disease Based Upon CAF Subtype

Decreased ER expression and estrogen responsiveness, coupled with gain of tamoxifen resistance are common indicators of increased metastatic potential in luminal breast cancer (Freund A, et al., *Oncogene*. 2003; 22(2):256-65; Garcia M, et al., *Proceedings of the National Academy of Sciences of the United States of America*. 1992; 89(23): 11538-42; Thompson E W, et al., *Journal of cellular physiology*. 1992; 150(3):534-44). Using RNAseq analysis, our data indicate that co-cultures of MCF7 or TAMR-1 cells with CD146$^{neg}$ CAFs, compared to co-cultures with CD146$^{pos}$ CAFs, have significantly decreased expression for genes associated with basement membrane integrity including COL4A1 (−3.9-fold and 7.0-fold), COL4A2 (4-fold and 3.2-fold), COL4A4 (2.4-fold and 3.4-fold), COL4A5 (90.5-fold and 59.7-fold) and COL4A6 (42.2-fold and 48.5-fold); in contrast, CD146$^{neg}$ CAF co-cultures have significantly increased expression of pro-migratory genes associated with matrix remodeling and invasion, including HBEGF (3.6-fold and 2.4-fold respectively), TNC (2.2-fold and 6-fold) and DDR2 (1.4-fold and 4.6-fold). Siegal et. al. demonstrated that loss of type IV collagens in breast cancer is associated with breast cancer invasion (Siegal G P, et al., *Invasion Metastasis*. 1981; 1(1):54-70). Interestingly, in colorectal cancer, Tanaka et. al. showed that specific loss of COL4A5 and COL4A6 protein expression is associated with invasive cancer and Ikeda et. al. later demonstrated promoter hypermethylation as one mechanism for this decreased expression (Ikeda K, et al., *The American journal of pathology*. 2006; 168(3):856-65). The significant 42- to 50-fold decrease in COL4A5 and COL4A6 in MCF7 co-cultures with CD146$^{neg}$ CAFs is in agreement with the data for colorectal cancer. Rearrangement of collagen fibers near the tumor edge from parallel to perpendicular is a hallmark of tumors with increased invasive/metastatic potential.

Figure 9:
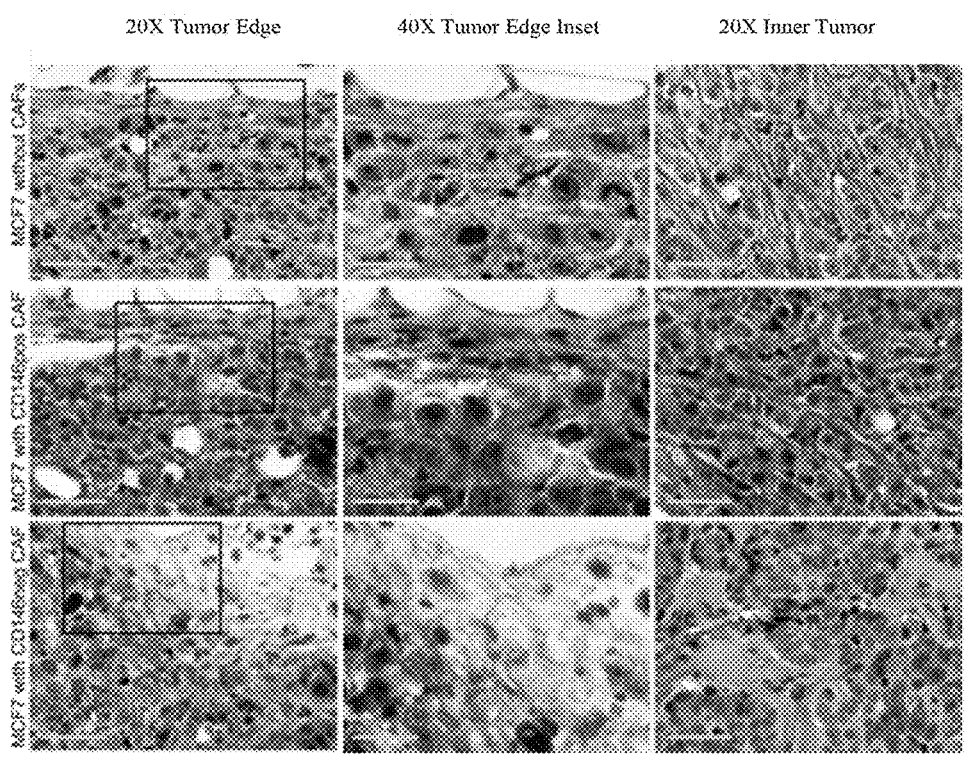
FIG. 9 is a set of nine images of MCF7 tumors that were grown in the mammary fat pad of immunodeficient mice (A upper three images) without CAFs, (B—middle three images) mixed with CD146$^{pos}$ CAFs or (C—lower three images) mixed with CD146$^{neg}$ CAB and stained with Gomori's Trichrome. The collagen deposition patterns for MCF7 alone and MCF7/CD146$^{neg}$ mixed tumors demonstrate intact tumor boarders with organized collagen fibers running parallel to the tumor edge. In contrast the collagen deposition patter for MCF7/CD146$^{neg}$ mixed tumor demonstrates a loss of intact tumor boarder with collagen fibers perpendicular to the tumor edge. Collagen lacks organization within the MCF7/CD146$^{neg}$ tumors.

Gomori's Trichrome staining of excised MCF7 tumors from mice without CAFs demonstrates increased collagen deposition within the tumor, with regions where the collagen fibers form barriers by completely encircle groups of tumor cells. Additionally, organized collagen fibers running parallel to the tumor border (FIG. 9). In comparison, tumors with CD146$^{neg}$ CAFs demonstrate a collagen pattern that is composed of disorganized, thick patches of fibers within the tumor that weave throughout the tumor but do not form barriers, furthermore, in addition to fibers running parallel to the tumor edge, long distinct fibers penetrate the tumor by aligning perpendicular to the tumor border. Tumors with CD146$^{pos}$ CAFs have a collagen pattern that is intermediate to the control and CD146$^{neg}$ CAF patterns. Within CD146$^{pos}$ CAF/MCF7 tumors, the collagen fibers are generally well organized and form some barrier regions by completely encircling tumor cells. The tumor border is mainly comprised of fibers aligning parallel to the tumor edge, but short perpendicular fibers are also present. These data show that our CAF subtypes promote important differences in collagen organization and deposition (FIG. 9).

The collagen receptor discoidin domain receptor proteins (DDR1 and DDR2) are unique receptor tyrosine kinases that utilize collagens as ligands. Cosmin M and colleagues demonstrated that over-expression of DDR2 inhibits fibrillogenesis, the process of collagen fibers organizing in long, fine fibrils. The thick collagen aggregates in MCF7/CD146$^{neg}$ CAF tumors are reminiscent of findings associated with DDR2 over-expression. Additionally, Zhang et, al, demonstrated that DDR2 activation stabilizes SNAI1 in breast cancer cells undergoing EMT, thereby promoting metastasis (Zhang K, et al., *Nat Cell Biol*, 2013; 15(6):677-87). Our RNAseq data indicates a 1.4-fold and 4.6-fold increase in DDR2 expression in MCF7 and TAMR-1 cells from CD146$^{neg}$ CAF compared to CD146$^{pos}$ CAF co-cultures without change in DDR1. Intriguingly, DDR2 expression increased according to tumor aggressiveness, with TAMR-1 cells being more aggressive than MCF7 cells. DDR2 activation induces up-regulation of MMP-1, -2 and -13 which further degrade the ECM and promote metastasis. Of the 25 genes coding MMPs, only 9 are significantly over-expressed in the epithelial and/or CAF component of MCF7/CD146$^{neg}$ co-cultures compared to MCF7/CD146$^{pos}$ CAF co-cultures. MMP-1, -2 and -13 are included in the list of 9, being over-expressed in the tumor cells co-cultured with CD146$^{neg}$ CAFs (MMP1: MCF7=6.6-fold, 117.8-fold TAMR-1; MMP2: MCF7=1.3-fold, TAMR-1=3.2-fold; MMP13: MCF7=6.5-fold, TAMR-1=no change).

Figure 10:
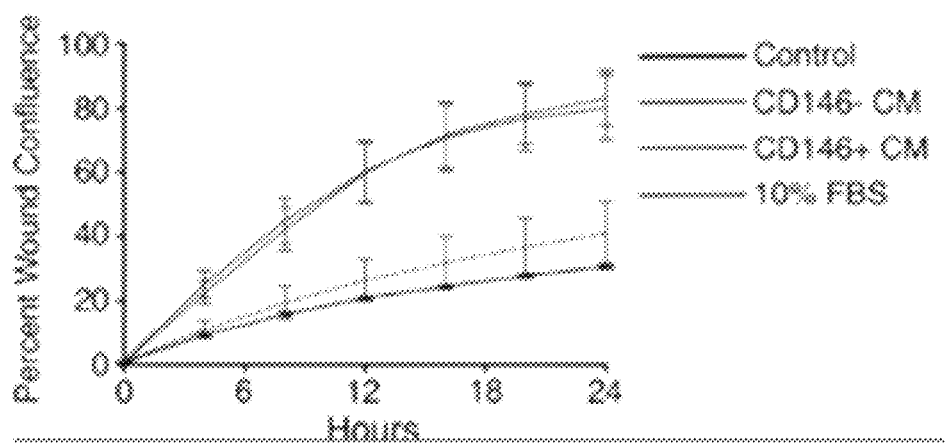
FIG. 10 is a pair of graphs illustrating (A) migration and (B) invasion scratch wound assays for MCF7 cells cultured in conditioned media from MCF7 cells, CD146$^{pos}$ CAFs or CD146$^{neg}$ CAFs. Both CAF subtype induce rapid migration but only CD146$^{neg}$ CAFs induce invasion through Matrigel. The invasion is inhibited by gefitibib (Geft) and is stimulated in CD146$^{pos}$ CAF conditioned media via addition of HBEGF. For (A) at the 24 hour time-point the plot lines from lowest to highest along the y-axis are as follows: Control; 10% FBS; CD146− CM; CD146+ CM. For (B) at the 24 hour time-point the plot lines from lowest to highest along the y-axis are as follows: Control; CD146− CM with Geft; CD146+ CM; CD146+ CM with HB-EGF; CD146+ CM CD146− CM.
Figure 10:
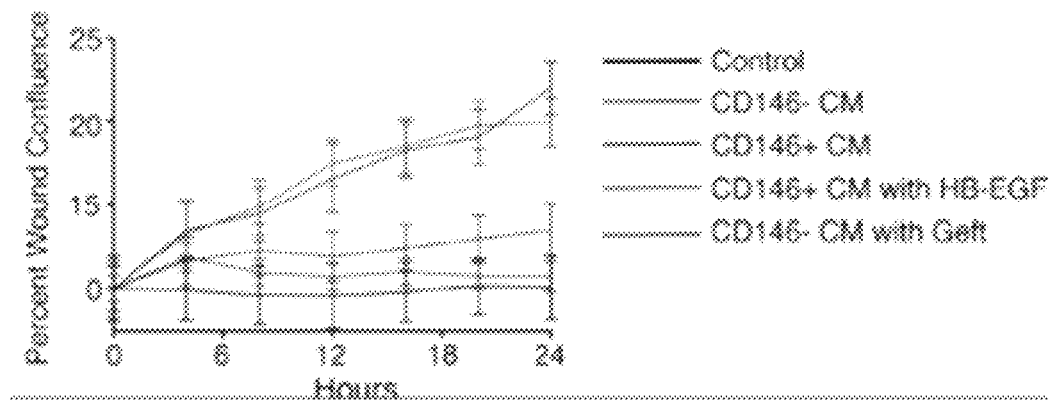

Finally, HBEGF is strongly associated with increased breast cancer metastasis and our data show that while conditioned media from both CAF subtypes induces significant migration of MCF7 cells, only CD146$^{neg}$ CAFs promote increased invasion. We successfully blocked CD146$^{neg}$ CAF induced invasion with the EGFR inhibitor gefitinib (FIG. 10). Taken together, our data show that CD146$^{neg}$ CAFs promote a more invasive tumor phenotype by significantly altering the extracellular matrix.

Figure 11:
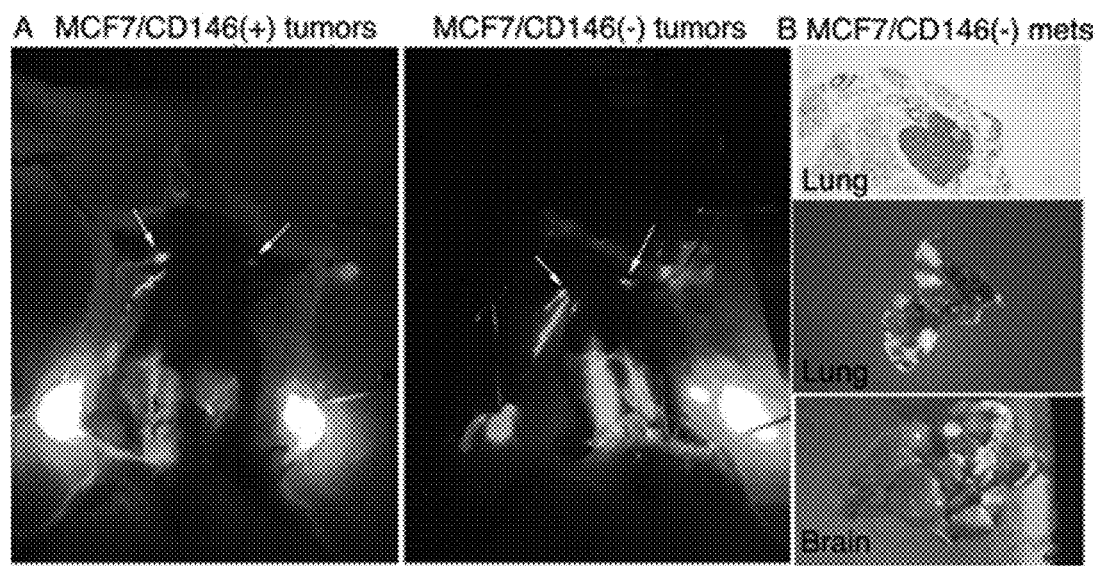
FIG. 11 is a set of five images (two images for (A) and three images for (B)) showing ZS-green labeled MCF7/CAF mixed orthotopic initiated tumors. (A) Representative images of metastatic spread to distal axial lymph nodes (white arrows) from the primary tumor mass in mice with MCF7/CD146$^{pos}$ CAFs and in mice with MCF7/CD146$^{neg}$ CAFs. (B) Representative images of lung and brain metastases from mice with MCF7/CD146$^{neg}$ CAFs.

A mixture of MCF7/CAFs (5×10^5 MCF7 labelled with Zsgreen and 10^6 CAFs) was implanted into the mammary fat pad of immunodeficient NSG mice (FIG. 11). After 10 weeks, the average tumor burden for mice with CD146$^{neg}$ CAFs was 570 mm^3 (range=174 mm^3 to 1048 mm^3). Four out of seven mice in the CD1.46$^{neg}$ CAF group had distant lymph node metastasis and 6 out of 7 had lung metastases. The mouse without lung metastasis in this group also lacked distant lymph node metastasis and had a tumor burden of 327 mm^3, which was not the smallest tumor in the group. Interestingly, 1 of the 7 CD146$^{neg}$ CAF mice had brain metastases, this animal had the smallest tumor burden in the group (174 mm^3). Interestingly, HBEGF has been shown to promote breast cancer brain metastasis. These data demonstrate that, similar to clinical outcomes, tumor burden does not necessarily predict the presence or absence of metastatic disease. In contrast to the mice with CD146$^{neg}$ fibroblasts, after 10 weeks, tumors were significantly smaller in both the group with CD146$^{neg}$ CAFs and in mice without CAFs (195 mm^3; range=51 to 312 mm^3 and 64.01 mm^3; range=26.36 mm^3 to 101 mm^3 respectively). Only two of six mice in the CD146$^{pos}$ group had distant lymph node metastasis and zero had lung or brain metastases. Control mice (4 of 4) were free of all metastases. These data demonstrate that both CAF subtypes can induce distant lymph node metastases, but CD146$^{neg}$ CAFs induce a much more aggressive metastatic phenotype as evidenced by time to metastasis and multiple organ involvement. These results can be further elaborated by: (1) expanding the model from a homogenous tumor cell population (MCF7 cells) to include ER+ tumors that are representative of clinical disease by using tissue collected from breast cancer patients; (2) determining if CD146$^{neg}$ CAF induced DDR2 expression and loss of type IV collagen are necessary and sufficient for extracellular matrix (ECM) remodeling and tumor progression; and, (3) determining if expression of HBEGF is necessary and sufficient for development of lung and brain metastases. The data presented herein allows for novel approach to modeling breast cancer metastasis that better accounts for the complexity of human disease and allows for the identification of potential drug targets in the tumor microenvironment.

Knowledge of the CAF subtypes in a patient tumor can determine the risk of developing metastatic disease and dictate use of compounds that inhibit the CD146$^{neg}$ CAF production of MMPs and tyrosine kinase inhibitors such that interrupting signaling through collagen receptor discoidin domain receptor proteins and EGFR as a means to prevent development of metastatic disease.

GLOSSARY OF CLAIM TERMS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "administration" and variants thereof (e.g., "administering" a compound) in reference to a compound of the invention means introducing the compound into the system of the subject in need of treatment. When a compound of the invention is provided in combination with one or more other active agents (e.g., a cytotoxic agent, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation or metastasis of the tumor. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

The term "endocrine therapy" refers to a treatment that adds, blocks, or removes hormones. More specifically, endocrine therapy with respect to breast cancer refers to treatments that target the estrogen receptor (ER) by blocking receptor binding with an antagonist or by depriving the tumor of estrogen. Endocrine therapy can also be referred to as anti-endocrine therapy, hormonal therapy, hormone therapy, and hormone treatment.

A "subject in need of treatment" is a mammal with cancer that is life-threatening or that impairs health or shortens the lifespan of the mammal.

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the preceding portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of treating cancer in a subject comprising the steps of:
   providing a sample containing stroma from cancerous tissue of the subject;
   screening the sample to detect the CD146(+)-to-CD146(−) ratio of fibroblasts in the stroma; and
   administering anti-endocrine therapy to the subject responsive to the detection of a high proportion of CD146(+) fibroblasts in the sample relative to a control.

2. The method according to claim 1 wherein the cancer is breast cancer.

3. The method according to claim 1 wherein the anti-endocrine therapy is provided by administering a compound selected from the group consisting of tamoxifen and fulvestrant.

4. A method of treating cancer in a subject comprising the steps of:
   providing a sample containing stroma from cancerous tissue of the subject;
   screening the sample to detect the CD146(+)-to-CD146(−) ratio of fibroblasts in the stroma; and
   administering a TGFβ inhibitor to the subject responsive to the detection of a high proportion of CD146(+) fibroblasts in the sample.

5. The method according to claim 4 wherein the cancer is breast cancer.

6. A method of treating cancer in a subject comprising the steps of:
   providing a sample containing stroma from cancerous tissue of the subject;
   screening the sample to detect the CD146(+)-to-CD146(−) ratio of fibroblasts in the stroma; and
   administering an EGFR inhibitor to the subject responsive to the detection of a high proportion of CD146(−) fibroblasts in the sample relative to a control.

7. The method according to claim 6 wherein the cancer is breast cancer.

8. The method according to claim 6 wherein the EGFR inhibitor is a compound selected from the group consisting of gefitinib, erlotonib, and cetuximab.

9. The method according to claim 1 wherein ratio of CD146(+)-to-CD146(−) is 60% CD146(+) to 40% CD146(−) or a higher CD146(+) percentage.

10. The method according to claim 9 wherein the cancer is breast cancer.

11. The method according to claim 9 wherein the anti-endocrine therapy is provided by administering a compound selected from the group consisting of tamoxifen and fulvestrant.

12. The method according to claim 4 wherein ratio of CD146(+)-CD146(−) is 60% CD146(+) to 40% CD146(−) or a higher CD146(+) percentage.

13. The method according to claim 12 wherein the cancer is breast cancer.

14. The method according to claim 6 wherein ratio of CD146(+)-to-CD146(−) is 20% CD146(+) to 80% CD146(−) or a lower CD146(+) percentage.

15. The method according to claim 14 wherein the cancer is breast cancer.

16. The method according to claim 14 wherein the EGFR inhibitor is a compound selected from the group consisting of gefitinib, erlotonib, and cetuximab.

* * * * *